United States Patent [19]

Morton, Jr.

[11] 4,243,592

[45] Jan. 6, 1981

[54] 9,11-DIDEOXY-10-OXA-TXB COMPOUNDS

[75] Inventor: Douglas R. Morton, Jr., Portage, Mich.

[73] Assignee: The Upjohn Company, Kalamazoo, Mich.

[21] Appl. No.: 19,752

[22] Filed: Mar. 12, 1979

[51] Int. Cl.$^3$ ............................................ C07D 319/04
[52] U.S. Cl. .............................. 260/340.7; 260/239 B; 260/326.36; 260/345.8 R; 544/148; 544/359; 546/207; 546/304; 560/112; 560/252; 568/660; 568/662
[58] Field of Search ...................................... 260/340.7

[56] References Cited

U.S. PATENT DOCUMENTS 3,505,386   4/1970   Babcock et al. .................. 260/340.7

FOREIGN PATENT DOCUMENTS 1046016 12/1958 Fed. Rep. of Germany ........ 260/340.7
1502385 10/1967 France ................................. 260/340.7
1151095  5/1969 United Kingdom ................. 260/340.7

OTHER PUBLICATIONS

Acker et al., Journ. Org. Chem., vol. 24, pp. 1162–1163.

*Primary Examiner*—Ethel G. Love
*Attorney, Agent, or Firm*—Robert A. Armitage

[57] ABSTRACT

The present specification discloses novel 9,11-dideoxy- or 9,11,15-trideoxy-10-oxa-thromboxane B compounds, their novel method of preparation and the pharmaceutical compositions and use thereof as antithrombotic, antiinflammatory, and antiasthma agents.

3 Claims, No Drawings

4,243,592

9,11-DIDEOXY-10-OXA-TXB COMPOUNDS

DESCRIPTION

1. Technical Field

The present invention relates to novel compositions of matter. Further, the present invention provides novel processes for preparing these compositions of matter. Moreover there are provided novel methods by which such compositions of matter are employed for pharmacologically useful purposes.

The present invention is specifically concerned with novel analogs of thromboxane $B_2$.

Structurally, thromboxane $B_2$ or $TXB_2$ has the structure and carbon atom numbering indicated by Formula I. As is apparent by reference to Formula I, $TXB_2$ may alternatively be named as 11a-homo-11a-oxa-$PGF_{2\alpha}$. For comparative purposes, the structure of $PGF_{2\alpha}$ or prostaglandin $F_{2\alpha}$ is provided in Formula II. For a discussion of the biological preparation of $TXB_2$, see Samuelsson, Proceedings of the National Academy of Sciences USA 71:3400–3404 (1974). For a discussion of the chemical production of thromboxane $B_2$ and numerous analogs thereof, see U.S. Pat. No. 4,070,384, issued 24 Jan. 1978.

For a detailed discussion of related prostaglandins, such as prostaglandin $F_{2\alpha}$ of formula II, see Bergstrom, et al., Pharmacological Reviews 20:1 (1968).

As is apparent by reference to Formulas I and II, both thromboxane $B_2$ and $PGF_{2\alpha}$ exhibit several asymmetric carbon atoms and these molecules may therefore exist in either racemic (optically inactive) form or in either of two optically active enantiomeric forms, i.e., the dextrorotatory and levorotatory forms. As represented in Formulas I and II, the particular optically active form of $TXB_2$ and $PGF_{2\alpha}$ obtained from biological sources is the enantiomer represented by these formulas. For convenience hereinafter use of the term thromboxane or "TXB" will refer to the optically active form of the thromboxane-type compound thereby referred to with the same absolute configuration as $TXB_2$ or $PGF_{2\alpha}$ obtained from biological sources.

The term "thromboxane intermediate" used herein refers to any heterocyclic or acyclic compound which is useful in preparing the various analogs of thromboxane $B_2$ disclosed herein. When a formula is used to depict a thromboxane intermediate, each such formula represents the particular stereoisomer of the thromboxane intermediate which is useful in preparing the TXB analog of the same relative stereochemical configuration as $TXB_2$ obtained from biological sources.

The term "thromboxane-type" (TXB-type) product, as used herein, refers to each of the various heterocyclic derivatives herein which are useful pharmacologically, as indicated hereinafter. The formulas, as drawn herein, which depict the thromboxane-type product, each represent the particular stereoisomer of that product which is of the same relative stereochemical configuration as $TXB_2$ obtained biosynthetically. The term "thromboxane analog", as used herein, refers to that stereoisomer of a TXB-type product which is of the same relative stereochemical configuration as $TXB_2$ obtained from biological sources or a mixture comprising that stereoisomer and the enantiomer thereof. In particular, where a formula is used to depict a thromboxane-type product herein, the term thromboxane analog refers to the compound of that formula or mixture comprising that compound and the enantiomer thereof. In formulas herein where a heterocyclic ring is not present, such a ring having been cleaved or to be introduced subsequently in further reaction steps, the convention by which substituents about asymmetric centers are depicted as either alpha or beta is as defined above, but with respect to the plane of the various atoms which comprise said ring before its cleavage or will comprise said ring as synthesized in the subsequent reaction steps.

2. Prior Art

As indicated above, thromboxane $B_2$ is known in the art. See Samuelsson, cited above. Likewise, numerous analogs of thromboxane $B_2$ and their use as reproductive cycle control agents is known in the art. See U.S. Pat. No. 4,070,384, issued 24 Jan. 1978.

Further, certain 11-oxa prostaglandin-type compounds are known in the art. See particularly Belgian Pat. No. 830,423 (Derwent Farmdoc CPI No. 01971X) and Tetrahedron Letters 43:3715–3718 (1975).

Other heterocyclic ring analogs of the prostaglandins include the 9α,11α- or 11α,9α-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

SUMMARY OF THE INVENTION

The present invention particularly provides:

(1) a thromboxane analog of formula III wherein $Y_1$ is (1) trans—CH=CH—,
(2) cis—CH=CH—,
(3) —CH$_2$CH$_2$—, or
(4) —C≡C—, wherein $M_1$ is α-$R_5$:β-OH, α-OH:β-$R_5$, or α-H:β-H, wherein $R_5$ is hydrogen or methyl;

wherein $L_1$ is α-$R_3$:β-$R_4$, α-$R_4$:β-$R_3$, or a mixture of α-$R_3$:β-$R_4$ and β-$R_3$:α-$R_4$, wherein $R_3$ and $R_4$ are hydrogen, methyl, or fluoro, being the same or different, with the proviso that one of $R_3$ and $R_4$ is fluoro only when the other is hydrogen or fluoro;

wherein $Z_1$ is (1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$—O—(CH$_2$)$_g$—CH$_2$—, or
(8) trans—CH$_2$—(CH$_2$)$_g$—CH$_2$—CH=CH—;
wherein g is one, 2, or 3;
wherein $R_7$ is (1) —(CH$_2$)$_m$—CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or (7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $X_1$ is
(1) —$COOR_1$, wherein $R_1$ is
  (a) hydrogen;
  (b) alkyl of one to 12 carbon atoms, inclusive;
  (c) cycloalkyl of 3 to 10 carbon atoms, inclusive;
  (d) aralkyl of 7 to 12 carbon atoms, inclusive;
  (e) phenyl;
  (f) phenyl substituted with one, two, or three chloro or alkyl of one to 3 carbon atoms;
  (g) phenyl substituted in the para position by
    (i) —NH—CO—$R_{25}$
    (ii) —CO—$R_{26}$
    (iii) —O—CO—$R_{27}$
    (iv) —CH=N—NH—CO—$NH_2$
    wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is phenyl or acetamidophenyl; inclusive, or a pharmacologically acceptable salt thereof when $R_1$ is hydrogen;
(2) —$CH_2OH$;
(3) —$COL_4$, wherein $L_4$ is
  (a) amino of the formula —$NR_{21}R_{22}$, wherein $R_{21}$ and $R_{22}$ are
    (i) hydrogen;
    (ii) alkyl of one to 12 carbon atoms, inclusive;
    (iii) cycloalkyl of 3 to 10 carbon atoms, inclusive;
    (iv) aralkyl of 7 to 12 carbon atoms, inclusive;
    (v) phenyl;
    (vi) phenyl substituted with one, 2, or 3 chloro, alkyl of one to three carbon atoms, inclusive, hydroxy, carboxy, alkoxycarbonyl of one to 4 carbon atoms, inclusive, or nitro;
    (vii) carboxyalkyl of 2 to 5 carbon atoms, inclusive;
    (viii) carbamoylalkyl of 2 to 5 carbon atoms, inclusive;
    (ix) cyanoalkyl of 2 to 5 carbon atoms, inclusive;
    (x) acetylalkyl of 3 to 6 carbon atoms, inclusive;
    (xi) benzoylalkyl of 7 to 11 carbon atoms, inclusive;
    (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
    (xiii) pyridyl;
    (xiv) pyridyl substituted by one, 2, or 3 chloro, alkyl of one to 3 carbon atoms, inclusive, or alkoxy of one to 3 carbon atoms, inclusive;
    (xv) pyridylalkyl of 6 to 9 carbon atoms, inclusive;
    (xvi) pyridylalkyl substituted by one, 2, or 3 chloro, alkyl of one to 3 carbon atoms, inclusive, hydroxy or alkoxy of one to 3 carbon atoms, inclusive;
    (xvii) hydroxyalkyl of one to 4 carbon atoms, inclusive;
    (xviii) dihydroxyalkyl of one to 4 carbon atoms, or
    (xix) trihydroxyalkyl of one to 4 carbon atoms with the further proviso that not more than one of $R_{21}$ and $R_{22}$ is other than hydrogen or alkyl;
  (b) cycloamino selected from the group consisting of
    (i) pyrrolidino,
    (ii) piperidino,
    (iii) morpholino,
    (iv) piperazino,
    (v) hexamethyleneimino,
    (vi) pyrrolino,
    (vii) 3,4-didehydropiperidinyl, or
    (viii) pyrrolidino, piperidino, morpholino, piperazino, hexamethyleneimino, pyrrolino, or 3,4-didehydropiperidinyl substituted by one or two alkyl of one to 12 carbon atoms, inclusive;
  (c) carbonylamino of the formula —$NR_{23}COR_{21}$, wherein $R_{23}$ is hydrogen or alkyl of one to 4 carbon atoms and $R_{21}$ is other than hydrogen, but otherwise as defined above; or
  (d) sulfonylamino of the formula —$NR_{23}SO_2R_{21}$, wherein $R_{21}$ and $R_{23}$ are as defined in (c);
(4) —$CH_2NL_2L_3$, wherein $L_2$ and $L_3$ are hydrogen or alkyl of one to 4 carbon atoms, inclusive, being the same or different, or a pharmacologically acceptable acid addition salt thereof wherein $X_1$ is —$CH_2NL_2L_3$;
(2) a thromboxane intermediate of formula IV, V, VI, VII, or VIII
wherein g, $L_1$, $M_1$, $R_7$, $X_1$, and $Y_1$ are as defined above
wherein n is the integer one or two and g is the integer one, two, or three;
wherein $M_7$ is $\alpha$-$R_5$:$\beta$-$OR_{10}$, $\alpha$-$OR_{10}$:$\beta$-$R_5$, or $\alpha$-H:$\beta$-H, wherein $R_{10}$ is a stable, acid hydrolyzable blocking group;
wherein $R_2$ is hydrogen or fluorine;
wherein $R_{12}$ is alkyl of one to 12 carbon atoms, inclusive, aralkyl of 7 to 12 carbon atoms, inclusive, aralkyl of 7 to 12 carbon atoms, inclusive; phenyl; or phenyl substituted with one, two, or three chloro or alkyl of one to 3 carbon atoms, and
wherein $R_{34}$ is a stable, hydrogenolyzable blocking group.

With regard to the divalent substituents described above (e.g., $L_1$ and $M_1$), these divalent radicals are defined as $\alpha$-$R_i$:$\beta$-$R_j$, wherein $R_i$ represents the substituent of the divalent moiety in the alpha configuration with respect to the ring and $R_j$ represents the substituent of the divalent moiety in the beta configuration with respect to the plane of the ring. Accordingly, when $M_1$ is defined as $\alpha$-OH:$\beta$-$R_5$, the hydroxy of the $M_1$ moiety is in the alpha configuration, i.e., as in $TXB_2$ above, and the $R_5$ substituent is in the beta configuration. Not all carbon atoms to which such divalent moieties are attached represent asymmetric centers. For example when both valence bonds are to hydrogen (e.g., $L_1$ or $M_1$ is $\alpha$-H:$\beta$-H), then no asymmetric center is present.

All the novel thromboxane analogs herein are named as 9,11-dideoxy-10-oxa-TXB compounds by virtue of the substitution of oxa for methylene at C-10 (refer to formula I) and the absence of hydroxyls at C-9 and C-11 which are present in thromboxane $B_2$. Moreover, when $M_1$ is $\alpha$-H:$\beta$-H, the thromboxane analogs are further described as 9,11,15-trideoxy-10-oxa-TXB compounds, since the C-15 hydroxy of thromboxane $B_2$ is also absent from such compounds.

When $R_5$ is methyl, the thromboxane analogs are all named as "15-methyl-TXB" compounds. Further, except for compounds wherein $Y_1$ is cis—CH=CH—, compounds wherein the $M_1$ moiety contains an hydroxyl in the beta configuration are additionally named as 15-epi-TXB compounds. For the compounds wherein $Y_1$ is cis—CH=CH—, then only compounds wherein the $M_1$ moiety contains an hydroxyl in the alpha configuration are named as 15-epi-TXB compounds. For a description of this convention of nomenclature for identifying C-15 epimers, see U.S. Pat. No. 4,016,184, issued 5 Apr. 1977, particularly columns 24-27 thereof.

Those TXB analogs herein wherein $Z_1$ is cis—CH=CH—CH$_2$—(CH$_2$)$_g$—CH$_2$— or cis—CH=CH—CH$_2$—(CH$_2$)$_g$—CF$_2$— are named as "TXB$_2$" compounds. The latter compounds are further characterized as "2,2-difluoro-TXB$_2$-type" compounds. When g is 2 or 3, the prostaglandin analogs so described are "2a-homo" or "2a,2b-dihomo" compounds, since in this event the $X_1$ terminated side chain contains 8 or 9 carbon atoms, respectively, in place of the 7 carbon atoms contained in PGF$_{2\alpha}$. These additional carbon atoms are considered as though they were inserted between the C-2 and C-3 positions. Accordingly, these additional carbon atoms are referred to as C-2a and C-2b, counting from the C-2 to the C-3 position.

Further, when $Z_1$ is —(CH$_2$)$_3$—(CH$_2$)$_g$—CH$_2$— or —(CH$_2$)$_3$—(CH$_2$)$_g$—CF$_2$—, wherein g is as defined above, the compounds so described are "TXB$_1$" comounds. When g is 2 or 3, the "2a-homo" and "2a,2b-dihomo" compounds are described as is discussed in the preceding paragraph.

When $Z_1$ is —CH$_2$—O—CH$_2$—(CH$_2$)$_g$—CH$_2$—, the compounds so described are named as "5-oxa-TXB$_1$" compounds. When g is 2 or 3, these compounds additionally so described as "2a-homo" or "2a,2b-dihomo" compounds, respectively, as discussed above.

When $Z_1$ is cis—CH$_2$—CH=CH—(CH$_2$)$_g$—CH$_2$—, wherein g is as defined above, the compounds so described are named "cis-4,5-didehydro-TXB$_1$" compounds. When g is 2 or 3, the compounds so described are further characterized as "2a-homo" or "2a,2b-dihomo" compounds, respectively, as discussed above.

When $Z_1$ is —(CH$_2$)$_2$—O—(CH$_2$)$_g$—CH$_2$, the compounds so described are named as "4-oxa-TXB$_1$" compounds. Similarly when $Z_1$ is trans—CH$_2$—(CH$_2$)$_g$—CH$_2$—CH=CH—, the compounds so described are "trans-2,3-didehydro-TXB$_1$" compounds.

The novel prostaglandin analogs herein which contain —(CH$_2$)$_2$—, cis—CH=CH—, or —C≡C— as the $Y_1$ moiety, are accordingly referred to as "13,14-dihydro", "cis-13", or "13,14-didehydro" compounds, respectively.

When $R_7$ is —(CH$_2$)$_m$—CH$_3$, wherein m is as defined above, the compounds so described are named as "19,20-dinor", "20-nor", "20-methyl" or "20-ethyl" compounds when m is one, 2, 4, or 5, respectively.

When $R_7$ is phenyl and neither $R_3$ nor $R_4$ is methyl, the compounds so described are named as "16-phenyl-17,18,19,20-tetranor" compounds, when s is zero. When $R_7$ is substituted phenyl, the corresponding compounds are named as "16-(substituted phenyl)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenyl or 16-(substituted phenyl)-18,19,20-trinor" compounds or "16-methyl-16phenyl- or 16-(substituted phenyl)-18,19,20-trinor" compounds, respectively.

When $R_7$ is phenylmethyl, the compounds so described are named as "17-phenyl-18,19,20-trinor" compounds. When $R_7$ is substituted phenylmethyl the corresponding compounds are named as "17-(substituted phenyl)-18,19,20-trinor" compounds.

When $R_7$ is phenylethyl the compounds so described as named as "18-phenyl-19,20-dinor" compounds, when s is 0. When s is one, 2, or 3, the corresponding compounds are named as "18-(substituted phenyl)-19,20-dinor" compounds.

When $R_7$ is phenylpropyl, the compounds so described are named as "19-phenyl-20-nor" compounds. When $R_7$ is substituted phenylpropyl the corresponding compounds are named as "19-(substituted phenyl)-20-nor" compounds.

When $R_7$ is phenoxy and neither $R_3$ nor $R_4$ is methyl, the compounds so described are named as "16-phenoxy-17,18,19,20-tetranor" compounds. When $R_7$ is substituted phenoxy the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy or 16-phenyl compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —CH$_2$OH, the compounds so described are named as "2-decarboxy-2-hydroxymethyl" compounds.

When $X_1$ is —CH$_2$NL$_2$L$_3$, the compounds so described are named as "2-decarboxy-2-aminomethyl or 2-(substituted amino)methyl" compounds.

When $X_1$ is —COL$_4$, the novel compounds herein are named as TXB-type, amides. Further, when $X_1$ is —COOR$_1$, the novel compounds herein are named as TXB-type, esters and TXB-type, salts.

Examples of phenyl esters substituted in the para position (i.e., $X_1$ is —COOR$_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamiophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., $X_1$ is —COL$_4$) include the following:

(1) Amides within the scope of alkylamino groups of the formula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyctopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, 2-phenylethylamide, and N-methyl-N-benzylamide. Amides within the scope of substituted phenylamido are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlroobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonaylbenzoylbutylamide, o-carboxybenzoylbutylamide, o-hydroxybenzoylmethylamide. Amides within the scope of pyridylamino are $\alpha$-pyridylamide, $\beta$-pyridylamide, and $\gamma$-pyridylamide. Amides within the scope of substituted pyridylamino are 4-methyl-$\alpha$-pyridylamide, 4-methyl-$\beta$-pyridylamide, 4-chloro-$\alpha$-pyridylamide, and 4-chloro-$\beta$-pyridylamide. Amides within the scope of pyridylalkylamino are $\alpha$-pyridylmethylamide, $\beta$-pyridylmethylamide, $\gamma$-pyridylmethylamide, $\alpha$-pyridylethylamide, $\beta$-pyridylethylamide, $\gamma$-pyridylethylamide, $\alpha$-pyridylpropylamide, $\beta$-pyridylpropylamide, $\gamma$-pyridylpropylamide, $\alpha$-pyridylbutylamide, $\beta$-pyridylbutylamide, and $\gamma$-pyridylbutylamide. Amides within the scope of substituted pyridylalkylamido are 4-methyl-$\alpha$-pyridylmethylamide, 4-methyl-$\beta$-pyridylmethylamide, 4-chloro-$\alpha$-pyridylmethylamide, 4-chloro-$\beta$-pyridylmethylamide, 4-methyl-$\alpha$-pyridylpropylamide, 4-methyl-$\beta$-pyridylpropylamide, 4-chloro-$\alpha$-pyridylpropylamide, 4-chloro-$\beta$-pyridylpropylamide, 4-methyl-$\alpha$-pyridylbutylamide, 4-methyl-$\beta$-pyridylbutylamide, 4-chloro-$\alpha$-pyridylbutylamide, 4-chloro-$\beta$-pyridylbutylamide, 4-methyl-$\beta$-pyridylbutylamide. Amides within the scope of hydroxyalkylamino are hydroxymethylamide, $\alpha$-hydroxyethylamide, $\beta$-hydroxyethylamide, $\alpha$-hydroxypropylamide, $\beta$-hydroxypropylamide, $\gamma$-hydroxypropylamide, 1-(hydroxymethyl)ethylamide, 1-(hydroxymethyl)propylamide, (2-hydroxymethyl)propylamide, and $\alpha,\alpha$-dimethyl-$\beta$-hydroxyethylamide. Amides within the scope of dihydroxyalkylamino are dihydroxymethylamide, $\alpha,\alpha$-dihydroxyethylamide, $\alpha,\beta$-dihydroxyethylamide, $\beta,\beta$-dihydroxyethylamide, $\alpha,\alpha$-dihydroxypropylamide, $\alpha,\beta$-dihydroxypropylamide, $\alpha,\gamma$-dihydroxypropylamide, $\beta,\beta$-dihydroxypropylamide, $\beta,\gamma$-dihydroxypropylamide, $\gamma,\gamma$-dihydroxypropylamide, 1-(hydroxymethyl)2-hydroxymethylamide, 1-(hydroxymethyl)-1-hydroxyethylamide, $\alpha,\alpha$-dihydroxybutylamide, $\alpha,\beta$-dihydroxybutylamide, $\alpha,\gamma$-dihydroxybutylamide, $\alpha,\delta$-dihydroxybutylamide, $\beta,\beta$-dihydroxybutylamide, $\beta,\gamma$-dihydroxybutylamide, $\beta,\delta$-dihydroxybutylamide, $\gamma,\gamma$-dihydroxybutylamide, $\gamma,\delta$-didihydroxybutylamide, $\delta,\delta$-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula —$NR_{23}COR_{21}$ are methylcarbonylamide, ethylcarbonylamide, phenylcarbonylamide, and benzylcarbonylamide.

(4) Amides within the scope of sulfonylamino of the formula —$NR_{23}SO_2R_{21}$ are methylsulfonylamide, ethylsulfonylamide, phenylsulfonylamide, p-tolylsulfonylamide, benzylsulfonylamide.

Exaples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of substituted phenoxy, phenylmethyl, phenylethyl, or phenylpropyl of the $R_7$ moiety are (o-, m-, or p-)tolyl, (o-, m-, or p-)ethylphenyl, 2-ethyltolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 2-ethyltolyloxy, 4-ethyl-o-tolyloxy, 5-ethyl-m-tolyloxy, (o-, m-, or p-)propylphenoxy, 2-propyl-(o-, m-, or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-dluoro-(o-, m-, or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3,4,5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenylmethyl, 2-ethyltolylmethyl, 4-ethyl-o-tolylmethyl, 5-ethyl-m-tolylmethyl, (o-, m-, or p-)propylphenylmethyl, 2-propyl-(o-, m-, or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(o-, m-, or p-)tolylmethyl, 4-fluoro-2,5-xylylmethyl, (2,4-, 2,5-, 2,6-, 3,4-, or 3,5-)difluorophenyl, (o-, m-, or p-)chlorophenylmethyl, 2-chloro-p-tolylmethyl, (3,4,5, or 6-)chloro-o-tolylmethyl, 4-chloro-2-propylphenylmethyl, 2isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-(trifluoromethylphenylmethyl, (o-, m-, or p-)methoxyphenylmethyl, (o-, m-, or p-)ethoxyphenylmethyl, (4- or 5-)chloro-2-methoxyphenylmethyl and 2,4-dichloro-(4- or 6-)methoxyphenylmethyl.

The novel TXB analogs of this invention are highly active as inhibitors of the thromboxane synthetase enzyme system. Accordingly, these novel compounds are useful for administration to mammals, including humans, whenever it is desirable medically to inhibit this enzyme system. For example, these novel compounds are useful as anti-inflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain in attained. When used for these purposes, these novel compounds cause fewer and lesser undesirable side effects than do the known synthetase inhibitors used to treat inflammation, for example, aspirin an indomethacin. When these novel compounds are administered orally, they are formulated as tablets, capsules, or as liquid preparations, with the usual pharmaceutical carriers, binders, and the like. For intravenous use, sterile isotonic solutions are preferred.

The novel TXB analogs of this invention are useful in the treatment of asthma, are useful, for example, as bronchodilators or as inhibitors of mediators, such as SRS-A and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories, parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The novel TXB analogs of this invention are useful in mammals, including man, as nasal decongestants and are used for this purpose, in a dose range of about 10 μg to about 10 mg per ml of a pharmacologically suitable liquid vehicle or as an aerosol spray, both for topical application.

These TXB analogs are useful whenever it is desired to inhibit-platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range of about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animals, to the perfused body portion, attached or detached, to the recipient, or to two or all of those at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

When $X_1$ is —COOR$_1$, the novel TXB analogs so described are used for the purposes described above in the free acid form, in ester form, in pharmacologically acceptable salt form. When the ester form is used, the ester is any of those within the above definition of $R_1$. However, it is preferred that the ester by alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopendylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basis amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When $X_1$ is —CH$_2$NL$_2$L$_3$, the novel TXB analogs so described are used for the purposes described above in either free base or pharmacologically acceptable acid addition salt form.

The acid addition salts of the 2-decarboxy-2-aminomethyl- or 2-(substituted aminomethyl)-TXB analogs provided by this invention, are the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the TXB analog with the stoichiometric amount of the acid corresponding to the pharmacologically acceptable acid addition salt.

To obtain the optimum combination of biological response specificity, potency, and duration of activity, certain compounds within the scope of this invention are preferred.

It is preferred that in the 8α-side chain g be either one or 3, especially one, i.e., the natural chain length of TXB$_2$. Further when the C-12 side chain contains —(CH$_2$)$_m$—CH$_3$, it is preferred that m be 3 or 4, most preferably 3. Further, it is preferred that, when $R_7$ is aromatic, $R_7$ be phenoxy, phenyl, or phenylmethyl, including substituted forms thereof. For those compounds wherein $R_7$ is substituted phenoxy or phenylalkyl, it is preferred there be only one or two substituents selected from the group consisting of chloro, fluoro, or trifluoromethyl. Further, for those compounds wherein $R_7$ is aromatic, it is preferred that $R_3$ and $R_4$ both be hydrogen.

Finally preferred are those compounds wherein $M_1$ is α-H:β-H.

Especially preferred are those compounds which satisfy two or more of the above preferences. Further, the above preferences are expressly intended to describe the preferred compounds within the scope of any generic formula of novel prostaglandin analogs disclosed herein.

The Charts herein describe methods whereby the novel prostaglandin analogs of this invention are prepared.

With respect to the Charts, n, g, $L_1$, $M_1$, $M_7$, $R_7$, $R_{12}$, $R_{34}$, $Y_1$, and $X_1$ are as defined above. $Z_4$ is n-butylboronyl; $R_{26}$ is alkyl, preferably methyl; and p is the integer $2-n$.

Those stable, acid hydrolyzable blocking groups within the scope of $R_{10}$ of the $M_7$ moiety are any group which replaces a hydroxy hydrogen and is neither attacked by nor as reactive to the reagents used in the transformations used herein as an hydroxy and which is subsequently replaceable with hydrogen in the preparation of the prostaglandin-type compounds. Several blocking groups are known in the art, e.g., tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include:
(a) tetrahydropyranyl;
(b) tetrahydrofuranyl;
(c) —C($OR_{21}$)($R_{22}$)—CH($R_{23}$)($R_{24}$), and
(d) —Si$R_{25}R_{26}R_{27}$,
wherein $R_{21}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, and wherein $R_{22}$ and $R_{23}$ are alkyl of 1 to 4 carbon atoms, inclusive, phenyl, phenyl substituted with 1, 2, or 3 alkyl of one to 4 carbon atoms, inclusive, or when $R_{22}$ and $R_{23}$ are taken together —$(CH_2)_a$— or —$(CH_2)_b$—O—$(CH_2)_c$, wherein a is 3, 4, or 5, or b is 1, 2, or 3, and c is 1, 2, or 3, with the proviso that b plus c is 2, 3, or 4, with the further proviso that $R_{22}$ and $R_{23}$ may be the same or different, wherein $R_{24}$ is hydrogen or phenyl; and wherein $R_{25}$, $R_{26}$, and $R_{27}$ are alkyl of one to 18 carbon atoms, inclusive, cycloalkyl of 3 to 10 carbon atoms, inclusive, aralkyl of 7 to 12 carbon atoms, inclusive, phenyl, or phenyl substituted with one to 3 alkyl of one to 4 carbon atoms, inclusive, being the same or different with at least one of $R_{25}$ $R_{26}$, and $R_{27}$ preferably being tertiary alkyl (most preferably t-butyl).

When the stable, acid hydrolyzable blocking group $R_{10}$ is tetrahydropyranyl, the tetrahydropyranyl ether derivative of the hydroxy of the TXB-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula

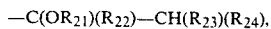
—C($OR_{21}$)($R_{22}$)—CH($R_{23}$)($R_{24}$), wherein $R_{21}$, $R_{22}$, $R_{23}$, and $R_{24}$ are as defined above, the appropriate reagent is a vinyl ether, e.g., isobutyl vinyl ether or any vinyl ether of the formula C($OR_{21}$)($R_{22}$)=C($R_{23}$)($R_{24}$), or an unsaturated cyclic or heterocyclic compound, e.g., 1-cyclohexen-1-yl methyl ether, or 4,5-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above. Finally, when the stable, acid hydrolyzable group is silyl, methods of preparation are those known in the art; see Pierce, "Silylation of Organic Compounds", Pierce Chemical Co., Rockford, Ill. (1968).

The blocking groups according to $R_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking groups is achieved. Optionally the silyl groups are removed by the methods of Corey, E.G., et al., JACS 94:6190 (1972), i.e., tetra-n-butyl-ammonium fluoride in THF.

$R_{34}$ is a stable, hydrogenolysable blocking group which is defined as any arylmethyl group which replaces the hydroxy hydrogen of the intermediates in the preparation of the various thromboxane analogs herein which is subsequently replaceable by hydrogen in the processes herein for preparation of these respective thromboxane analogs, being stable with respect to the various reactions to which intermediates therefor are subjected and being introduced and subsequently removed by hydrolgenolysis under conditions which yield substantially quantitative yields of desired products.

Examples of such arylmethyl groups are
(a) benzyl;
(b) benzyl substituted by one to 5 alkyl of one to 4 carbon atoms, inclusive, chloro, bromo, iodo, fluoro, nitro, phenylalkyl of 7 to 12 carbon atoms, inclusive, with the further proviso that the various substituents are the same or different;
(c) benzhydryl;
(d) benzhydryl substituted by one to 10 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings;
(e) trityl;
(f) trityl substituted by one to 15 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings.

The introduction of such ether linkages to the hydroxy-containing precursors therefor proceeds by methods known in the art, for example by reaction of the hydroxy-containing compound with the benzyl or substituted benzyl halide (chloride, bromide, or iodide) corresponding to the desired ether. This reaction proceeds in the presence of an appropriate condensing agent (e.g., silver oxide). The mixture is stirred and heated to 50° to 80° C. Reaction times of 4 to 20 hours are ordinarily sufficient.

These arylmethyl groups are subsequently removed by hydrogenolysis, for example by catalytic hydrogenation over a 5–10 percent palladium-on-carbon catalyst. See U.S. Pat. No. 4,070,384 for examples of such groups and their use in the synthesis of thromboxane analogs.

With further respect to Chart A, the formula XXI compounds are described by Kelly, R.C., et al., "Synthesis of Thromboxane $B_2$", Tetrahedron Letters 37:3279–3282 (1976) and in U.S. Pat. No. 4,070,384.

The formula XXII compound is prepared from the formula XXI compound by conventional esterification methods. For example, methods known in the art for the esterification of prostaglandins, (e.g., those described in U.S. Pat. No. 4,016,184) are employed. Thus, etherial diazoalkanes or alkyiodides are employed when $R_1$ is alkyl. For utmost convenience in the synthesis of Chart A, preferred esters are simple alkyl esters, most preferably methyl.

The formula XXIII compound is then prepared from the formula XXII compound by glycolization. Particularly useful reagents in accomplishing this glycolization are osmium tetraoxide in a suitable solvent (e.g., alcohol) and N-methylmorpholine N-oxide dihydrate. This glycolization is accomplished by methods analogous to those described in U.S. Pat. No. 4,020,173, see particularly, the discussion in this patent at column 18.

Thereafter the formula XXIII product is converted to the formula XXIV compound by oxidation with lead tetra-acetate followed by reduction with lithium aluminum hydride. This oxidation proceeds by methods analogous to those known in the art, see especially U.S. Pat. No. 4,070,384, column 58, and U.S. Pat. No. 4,020,173 (Example 17, column 44).

The formula XXIV compound is then transformed to the formula XXV compound by n-butylboronation. This reaction proceeds by methods known in the art, i.e., reacting the formula XXIV compound with a slight excess of n-butylboronic acid at elevated temperatures. This cyclic n-butylboronization procedure is described at columns 73–74 of U.S. Pat. No. 4,016,184.

Thereafter the formula XXV compound is converted to the formula XXVI compound by esterification. In accomplishing this reaction, conventional esterification methods are employed. For example, the acid chloride corresponding to the desired ester in a tertiary amine solvent (e.g., pyridine) is employed. With regard to the convenience of the synthesis of Chart A, preferred esters are the alkanoates, e.g., the pivalate.

Thereafter the formula XXVII compound is prepared from the formula XXVI compound by decycloboronization. In accomplishing this reaction an alkali metal hydroxide, carbonate, or bicarbonate (e.g., sodium bicarbonate, or lithium, or potassium hydroxide) is combined with the formula XXVI compound in an alcohol. See again U.S. Pat. No. 4,016,184 for a description of the instant decycloboronization.

Thereafter, the formula XXVII compound is transformed to the formula XXVIII compound by acetal cyclization. For this purpose, dimethoxymethane is employed with a catalytic amount of acid (e.g., p-toluenesulfonic acid monohydrate). The reaction proceeds at reflux temperatures and is ordinarily complete within several hours. Suitable organic solvents (e.g., benzene or toluene) are employed and the formula XXVIII product is recovered by conventional means.

Finally with respect to Chart A, the formula XXIX compound is prepared from the formula XXVIII compound by catalytic hydrogenolysis.

With respect to Chart B, the formula XXXI compound prepared in Chart A is transformed to the formula XXXIV intermediate exhibiting a fully elaborated C-12 side chain. Reaction sequence of Chart B is accomplished by methods known in the art.

Firstly, the formula XXXI compound is transformed to the formula XXXII compound by methods described in U.S. Pat. Nos. 4,016,184 and 4,112,224. Regarding these U.S. Patents, the former particularly describes methods for preparing the formula XXXII compound wherein $M_1$ contains an hydroxyl group, while the latter describes methods for preparing compounds wherein $M_1$ is $\alpha$-H:$\beta$-H.

Further with regard to U.S. Pat. No. 4,016,184, see the reaction sequence of Chart A therein where the formula XV compound is converted to the corresponding formula XIX compound. Regarding U.S. Pat. No. 4,112,224, see the reaction sequence of Chart A wherein the formula XXXIX compound is dehydroxylated at the C-15 position to the formula XXXI compound or Chart B (formula XLII-XLIV), where the C-12 side chain is introduced without the hydroxyl functionality being present.

The thromboxane analogs herein with fully elaborated C-12 chains are prepared from corresponding aldehydes of the formula XXXI compound by Wittig oxoalkylation. Reagents for such oxoalkylations known in the art or prepared by methods known in the art are employed. See for reference D. H. Wadsworth, et al., Journal of Organic Chemistry 30, 680 (1965). In the preparation of such thromboxane intermediates with elaborated C-12 side chains, certain phosphonates are employed in the Wittig reaction. These phosphonates are of the general formula $(R_{15}O)_2-PO-CH_2-CO-C(L_1)-R_7$ wherein $L_1$ and $R_7$ are as defined above and $R_{15}$ is alkyl of one to 8 carbon atoms, inclusive.

Phosphonates of the above general formula are prepared by methods known in the art. See Wadsworth, et al., as cited above. Conveniently the appropriate aliphatic acid ester is condensed with the anion of dimethyl methylphosphonate as produced using n-butyllithium. For this purpose, acids of the general formula: $HOOC-C(L_1)-R_7$ are employed in the form of their lower alkyl esters, preferably methyl or ethyl. The methyl esters for example are readily obtained by reaction of the corresponding acids with diazomethane.

For example, when $R_7$ is phenoxy or substituted phenoxy and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichlorophenoxy-, (4- or 6-)chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted)phenoxypropionic acids, which are useful in the preparation of the above acids whrein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy-, (o-, m-, or p-

)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is phenyl, or phenylalkyl, or substituted phenyl, or phenylalkyl.

For example, when $R_7$ is phenylmethyl or substituted phenylmethyl and $R_3$ and $R_4$ of the $L_1$ moiety are both hydrogen, there are available to following phenyl or substituted phenyl propionic acids: (o-, m-, or p-)chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl and $R_7$ is phenylmethyl or substituted phenylmethyl, there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl and $R_7$ is phenylmethyl or substituted phenylmethyl there are available, for example, the following 2,2-dimethyl-3-phenyl or substituted phenyl propionic acids: phenyl- and p-methylphenyl.

When one and only one of $R_3$ and $R_4$ is fluoro and $R_7$ is phenylmethyl or substituted phenylmethyl, there is available, for example, 2-fluoro-3-phenyl propionic acid.

Phenyl substituted acids (as above wherein $R_7$ is aralkyl) are prepared by methods known in the art, for example, by reacting a mixture of the appropriate methyl- or fluoro-substituted acetic acid, with a solution of a secondary amine (e.g., diisopropylamine), and n-butyllithium in an organic diluent (e.g., tetrahydrofuran) with the appropriately substituted benzyl chloride. The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when one of $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e., butyric, pentanoic, hexanoic, heptanoic, and octanoic. The transformation of these 2-oxoalkanoic acids to the corresponding 2,2-difluoro alkanoic acids proceeds by methods known in the art, using known ketonic fluorinating reagents. For example, $MoF_6 \cdot BF_3$ is advantageously employed in the fluorination.

The trans-enone ester product of the Wittig reaction may then be catalytically hydrogenated ($Y_1$ is $-CH_2CH_2-$) photo isomerized ($Y_1$ is cis—CH═CH—), or dihalogenated-didehydrohalogenated ($Y_1$ is $-C\equiv C-$) depending upon the desired formula XXXII product.

The oxo group introduced by Wittig oxoalkylation is then reduced to the $M_1$ moiety by known methods.

The above 3-oxo compound is transformed to the corresponding 3'α or 3'β-hydroxy cyclic acetal lactone, wherein $M_1$ is α-H:β-OH or α-OH:β-H by reduction of the 3'-oxo moiety, followed by optional separation of the 3'α- and 3'β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium (tri-t-butoxy)-aluminum hydride, metal tri-alkyl borohydrides, e.g., sodium trimethoxy borohydride, lithium borohydride, and the like. In those cases in which carbon-carbon double bond reduction need not be avoided, the boranes, e.g., disiamylborane (bis-3-methyl-2-butyl borane) are alternatively employed.

For the production of C-15 epimerically pure thromboxane analogs, the 15-epi compound is separated from the mixture by methods known in the art. For example, silica gel chromatography is advantageously employed.

The 3'-oxo compound is transformed into the corresponding (3'RS)-3'-methyl cyclic acetal ester wherein $M_1$ is a mixture of α-CH$_3$:β-OH and α-OH:β-CH$_3$ by reaction of the 3-oxo compound with a Grignard reagent, CH$_3$MgHal, wherein Hal is chloro, bromo, or iodo. The Grignard complex is thereafter hydrolyzed, for example, using saturated aqueous ammonium chloride as is known in the art. An alternate method for transforming the 3-oxo compound to a (3'RS)-3'-methyl compound is by reaction of the 3'-oxo compound with trimethylaluminum.

The preferred method for separation of these (3'RS)-3'-methyl epimers is by separation of the corresponding C-15 epimers of the TXB-type, methyl esters using silica gel chromatography or high presssure liquid chromatography (HPLC).

Finally when $M_1$ is α-H:β-H the 3'α- or 3'β- hydroxy compound is deoxygenated by first derivatization (e.g., to a silyl ether), then reductively deoxygenated (e.g., lithium metal in the presence of a primary amine). See U.S. Pat. No. 4,112,224 for detailed procedures.

Thereafter the formula XXXII compound is transformed to the formula XXXIII compound (when $M_1$ contains an hydroxyl group) by etherification. The desired ether functionality is introduced by methods hereinabove described.

Thereafter, the formula XXXIII compound is transformed to the formula XXXIV compound by saponification, under basic conditions, of the ester. Methods employed are those known in the art for saponifying acyl protecting groups, e.g., an alkali metal carbonate or hydroxide (potassium carbonate or hydroxide in methanol) or methanolic sodium methoxide are employed.

Thereafter the formula XXXIV alcohol is oxidized to the formula XXXV compound by methods known in the art, e.g., Moffatt oxidation or Collins oxidation in situ. Finally the formula XXXVI compound is prepared by hydrolysis (when $M_1$ is not $\alpha$-H:$\beta$-H) of the formula XXXV compound by methods hereinabove described.

Chart C describes a method whereby the formula XLI compound is transformed to the formula XLIII products wherein $Z_1$ is —$CH_2$—O—$CH_2$—($CH_2$)$_g$—$CH_2$—. In this regard, the formula XLI compound is transformed to the formula XLII compound where $X_1$ is —$COOR_1$ by etherification methods described in U.S. Pat. No. 3,931,279. Thereafter, the corresponding alcohols ($X_1$ is —$CH_2OH$) are prepared by lithium aluminum hydride reduction (in accordance with methods described in U.S. Pat. No. 4,028,419), amines, ($X_1$ is —$CH_2NL_2L_3$) by amination methods described in U.S. Pat. No. 4,073,808), or amides ($X_1$ is —$COL_4$) by methods described in U.S. Pat. No. 4,100,192.

Thereafter the formula XLIII product is prepared from the formula XLII compound by hydrolysis of the $R_{10}$ ether, if any, by methods described above.

Chart D provides a method whereby the formula LI compound of Chart A is transformed to the formula LV thromboxane analogs of formula III, wherein $Z_1$ is —($CH_2$)$_2$—O—($CH_2$)$_g$—$CH_2$—. With respect to Chart D, the formula LII enol ether is prepared from the formula LI compound by a Wittig alkylation in accordance with methods known in the art. With respect to Chart D, $R_{26}$ is preferably a simple ether linkage, e.g., lower alkyl. In accomplishing this Wittig alkylation, the formula LI compound is first oxidized to the corresponding aldehyde, by methods known in the art (e.g., a Collins or Moffatt oxidation), and thereafter reacted with the alkoxymethylenetriphenylphosphorane Wittig reagent. Methodology for this reaction is described in U.S. Pat. No. 4,016,184 at column 61. Thereafter the enol ether is hydrolyzed to its formula LIII aldehyde form by methods known in the art, e.g., treatment with strong mineral acid.

Thereafter the formula LIII compound is transformed to the formula LIV compound by $R_{10}$ etherification procedures (when $M_1$ is not $\alpha$-H:$\beta$-H) analogous to those described in Chart B for the conversion of the formula XXXII compound to the formula XXXIII compound. This formula LIV compound is then reduced to its corresponding primary alcohol (Formula LIV) by known methods (e.g., sodium borohydride) and thereafter converted to the formula LV product by methods analogous to those of Chart C.

With respect to Chart E, the formula LXI aldehyde prepared in Chart D is transformed to the formula LXIII products or the formula III compounds wherein $Z_1$ is
cis—CH=CH—$CH_2$—($CH_2$)$_g$—$CH_2$—,
cis—CH=CH—$CH_2$—($CH_2$)$_g$—$CF_2$—,
cis—$CH_2$—CH=CH—($CH_2$)$_g$—$CH_2$—,
—($CH_2$)$_3$—($CH_2$)$_g$—$CH_2$—, or
—($CH_2$)$_3$—($CH_2$)$_g$—$CF_2$.

The reaction sequence in Chart E is undertaken by methods known in the art. The formula LXII compound wherein $X_1$ is a carboxylic acid is prepared by Wittig alkylation procedures known in the art. For a general description of the preparation of such carboxylic acids, see methods disclosed in U.S. Pat. No. 4,073,808, especially the preparation of the formula XLIV compound in Chart A therein.

Thereafter the formula LXIII compound is prepared from the formula LXII compound by selective catalytic hydrogenation, again employing methods known in the art. In this regard, the reaction is analogous described in the preparation of the formula XXXV compound from the formula XXXIV compound in Chart A of U.S. Pat. No. 4,073,808.

Chart F provides a preferred method, however, whereby the formula LXIII compounds of Chart E are prepared. With respect to Chart F, the formula LXXI compound, prepared above, is saponified to the formula LXXII compound by methods described hereinabove. Thereafter, the formula LXXII alcohol is oxidized to the corresponding aldehyde and thereafter Wittig $\omega$-carboxyalkylated and catalytically hydrogenated and hydrogenolyzed to the formula LXXIII compound. In this regard, the reaction sequence is substantially identically to that described in Chart A (Part V) of U.S. Pat. No. 4,070,384, wherein in the formula XXXV compound is Wittig alkylated and catalytically hydrogenated and hydrogenolyzed to the formula XXXVII compound therein.

The formula LXXIII compound thusly prepared is thereafter converted to the formula LXXIV compound by methods described in Chart B for the preparation of the formula XXXII compound from the formula XXXI compound.

Finally, Chart G provides a method whereby the formula LXXXI compound prepared above is transformed to the corresponding trans-2,3-didehydro compounds of formula LXXXIV.

The formula LXXXII compound is prepared from the formula LXXXI compound by $\alpha$-phenylselenidization. Accordingly, the preparation of this formula LXXXII phenylselenidyl derivative, the formula LXXXI compound is first reacted with a lithio-N-isopropylcyclohexylamide, thereby generating the C-2 anion corresponding to formula LXXXII. Thereafter this anion is reacted with diphenylselenide, yielding the formula LXXXII compound.

Thereafter, the formula LXXXII compound is hydrolyzed to the formula LXXXIII compound, employing methods described above, i.e., acidic conditions. This formula LXXXIII compound is then transformed to the formula LXXXIV compound by dehydrophenylselenidization, yielding the trans-2,3-didehydro product. Thereafter, the carboxy-containing compound is transformed to the $X_1$-containing compound of formula LXXXV by methods described above.

Accordingly, the various compounds in accordance with the present invention are all prepared by the methods in the charts above.

DESCRIPTION OF THE PREFERRED EMBODIMENTS

The present invention is more fully understood by the following examples:

EXAMPLE 1

4$\beta$-Hydroxymethyl-5$\alpha$-(2'-hydroxymethyl-1,3-dioxane, 2'-pivalate (Formula XXIX: $R_{12}$ is t-butyl)

Refer to Chart A.

A. 5$\alpha$-carbomethoxymethyl-6$\beta$-benzyloxymethyl-5,6-dihydro-1,2-pyrone (Formula XXII: $R_1$ is methyl and $R_{34}$ is benzyl).

A solution of 8.92 g of 5$\alpha$-carboxymethyl-6$\beta$-benzyloxymethyl-5,6-dihydro-1,2-pyrone (Formula XXI:

$R_{34}$ is benzyl) in 200 ml of acetonitrile is treated with 12.4 ml of diisopropylethylamine in 17.7 ml of methyl iodide. The reaction mixture is then stirred at ambient temperature for 4 hr, diluted with brine and 0.5 M aqueous potassium bisulfate, and extracted with ethyl acetate. The combined organic extracts are then washed with brine, saturated aqueous sodium bicarbonate, brine, and dried over sodium sulfate. Concentration under reduced pressure yields 9.33 g of crude formula XXII compound. Chromatography on 360 g of 70-230 mesh silica gel (packed and eluted with ethyl acetate in Skellysolve B; 2:3) yields 8.4 g of pure formula XXII product. NMR absorptions are observed at 2.40-2.67, 3.13, 3.68, 3.66-3.9, 4.3-4.65, 4.57, 5.98, 6.83, and 7.32δ (deuterochloroform solvent). Infrared absorptions are observed at 1735, 1605, 1585, 1495, 1250, 1235, 1170, 1130, 1100, 1040, 815, 745, and 700 cm$^{-1}$. The mass spectrum exhibits a high resolution molecular ion at 290.1160.

B. (3RS,4RS)-3,4-dihydroxy-5α-carbomethoxymethyl-6β-benzyloxymethyl-3,4,5,6-tetrahydro-1,2-pyrone (Formula XXIII: $R_1$ is methyl and $R_{34}$ is benzyl). A solution of 0.95 g of the reaction product of Part A in 10 ml of acetone and 1 ml of water is treated with 4 ml of a solution of osmium tetraoxide in t-butanol (20 mg/ml concentration) and 0.75 g of N-methylmorpholine-N-oxide dihydrate. The reaction mixture is then stirred at ambient temerature for 30 min. Thereafter the resulting solution is then diluted with brine and extracted with ethyl acetate. The organic extracts are then washed with brine, dried over sodium sulfate, and concentrated under reduced pressure to yield 1.02 g of crude formula XXIII product as a pale yellow oil. Chromatographing with 60 g of 70-230 mesh silica gel packed and eluted with 15% acetone in methylene chloride yields 0.55 g of pure formula XXIII compound. NMR absorptions are observed at 2.1-2.9, 3.6-4.0, 3.66, 4.22, 4.54, 4.3-4.65, and 7.29δ (deuterochloroform solvent). Infrared absorptions are observed at 3460, 1740, 1610, 1585, 1495, 1215, 1175, 1125, 1105, 740, and 700 cm$^{-1}$. The mass spectrum for the trimethylsilyl derivative exhibits a high resolution molecular ion at 468.2001. Silica gel TLC $R_f$ is 0.25 in 15% acetone in methylene chloride.

C. (2S,3S)-3-hydroxymethyl-1,2,5-trihydroxypentane, 1-(benzylethyl) (Formula XXIV: $R_{34}$ is benzyl). A solution of 0.50 g of the reaction product of Part B in 42 ml of benzene is treated with 0.685 g of lead tetraacetate. The reaction mixture is then stirred at ambient temperature for 45 min, diluted with brine, and extracted with ethyl acetate. The organic extracts are then washed with water and brine, dried over sodium sulfate, and concentrated under reduced pressure to yield a colorless oil. The oil is then dissolved in 10 ml of tetrahydrofuran and added to a suspension of 0.175 g of lithium aluminum hydride in 10 ml of tetrahydrofuran (cooled to 0° C.). The resulting mixture is then stirred at 0°-25° C. for 3 hr. Excess reducing agent is then quenched by dropwise addition of 0.18 ml of water, 0.18 ml of 15% aqueous sodium hydroxide, and 0.54 ml of water. The resulting mixture is then filtered through diatomaceous earth, washed with tetrahydrofuran and concentrated under reduced pressure to yield 0.289 g of crude formula XXIV compound as a colorless oil. Chromatography on 25 g of 70-230 mesh silica gel packed and eluted with 40% acetone in methylene chloride yields 0.185 g of pure formula XXIV product as a colorless oil. NMR absorptions are observed at 1.5-2.0, 3.33, 3.45-4.13, 4.57, and 7.33δ (deuterochloroform solvent). Infrared absorptions are observed at 3350, 1450, 1366, 1209, 1074, 1054, 1026, 738, and 700 cm$^{-1}$. The mass spectrum for the trimethylsilyl derivative exhibits a high resolution molecular ion at 456.2564 and other peaks at 441, 349, 335, 276, 245, 155, 103, and 91. Silica gel TLC $R_f$ is 0.22 in acetone and methylene chloride (1:1).

D. (2S,3S)-3-hydroxymethyl-1,2,5-trihydroxypentane, 1-(benzylether), 5-pivalate (formula XXVII: $R_{12}$ is t-butyl and $R_{34}$ is benzyl). A mixture of 0.79 g of the reaction product of Part C, 40 ml of methylene chloride and 0.37 g of n-butylboronic acid is heated with stirring at 50°-55° C. Distilled methylene chloride is replaced in quantities of 2.5 ml in order to maintain constant reaction volume. After 2.5 hr the reaction mixture is then cooled to 10° C. and treated with 1.38 ml of triethylamine in 0.61 ml of pivaloyl chloride. The reaction mixture is then stirred at 10°-25° C. for 3.5 hr and thereafter at −14° C. for 48 hr. An additional 1.38 ml of triethylamine in 0.61 ml of pivaloyl chloride is then added and stirring continued at 0°-25° C. for 3.5 hr. The resulting mixture is then treated with 1.4 ml of triethylamine and 1.4 ml of 85% aqueous lactic acid. After stirring for 10-15 min, the reaction mixture is diluted with brine and extracted with ethyl acetate. The combined organic extracts are then washed with ice cold 0.5 M aqueous potassium bisulfate, saturated aqueous sodium bicarbonate, and brine, dried over sodium sulfate, and concentrated under reduced pressure to yield 1.6 g of a tan-colored oil, crude formula XXVI compound. This oil is then dissolved in 20 ml of methanol, 4.0 ml of 30% aqueous hydrogen peroxide and 4.0 ml of saturated aqueous sodium bicarbonate. The resulting mixture is then stirred at ambient temperature for 30 min, diluted with brine, and extracted with ethyl acetate. The organic extracts are then washed with water and brine, dried over sodium sulfate, and concentrated under reduced pressure to yield crude formula XXVII compound as a pale yellow oil. Chromatographing on 55 g of 70-230 mesh silica gel packed with 10% acetone in methylene chloride and eluting with 10-20% acetone in methylene chloride yields 0.652 g of pure formula XXVII product as a colorless oil. NMR absorptions are observed at 1.18, 1.75, 3.02, 3.48-4.0, 4.14, 4.57 and 7.34δ (deuterochloroform solvent). Infrared absorptions are observed at 3438, 1727, 1483, 1454, 1401, 1368, 1288, 1167, 1104, 1030, 740, and 703 cm$^{-1}$. The mass spectrum for the trimethylsilyl derivative exhibits a high resolution peak at 257.1530 and other peaks at 242, 217, 173, 159, 155, 143, 103, 91 and 57. Silica gel TLC $R_f$ is 0.46 in acetone and methylene chloride (3:7).

E. 4β-benzyloxymethyl-5α-(2′-hydroxyethyl)-1,3-dioxane, 2′-pivalate (formula XXVIII: $R_{12}$ is t-butyl and $R_{34}$ is benzyl). A solution of 0.724 g of the reaction product of Part D, 25 ml of toluene, 1.97 ml of dimethoxymethane, and 0.04 g of p-toluenesulfonic acid monohydrate is stirred at 25° C. for 1.5 hr. Thereafter, an additional 0.056 g of p-toluenesulfonic acid monohydrate is added and stirring continued for 2 hr. Additional dimethoxymethane (1.97 ml) is then added and the reaction mixture stirred again at 25° C. for 1.5 hr, followed by stirring at reflux for 2 hr. Thereafter the reaction mixture is cooled, diluted with brine, and extracted with ethyl acetate. The organic extracts are then washed with saturated aqueous sodium bicarbonate, and brine, dried over sodium sulfate, and concentrated under reduced pressure to yield 0.724 g of crude formula XXVIII product as a pale yellow oil. Chromatographing on 75 g of 70–230 mesh silica gel packed and eluted with 25% ethyl acetate in Skellysolve B yields 0.55 g of pure formula XXVIII product as a colorless oil. NMR absorptions are observed at 1.18, 1.2–2.5, 3.13–3.73, 4.02, 4.0–4.11, 4.58, 4.64, 5.08, and 7.31δ (deuterochloroform solvent). Infrared absorptions are observed at 1726, 1481, 1454, 1401, 1365, 1285, 1184, 1156, 1084, 1044, 943, 742, and 704 cm$^{-1}$. Silica gel TLC R$_f$ is 0.26 in ethyl acetate and Skellysolve B (1:3).

F. 4β-hydroxymethyl-5α-(2′-hydroxyethyl)-1,3-dioxane, 2′-pivalate (Formula XXIX: R$_{12}$ is t-butyl). A mixture of 0.548 g of the reaction product of Part E, 10 ml of 95% aqueous ethanol and 0.25 g of 10% palladium-on-carbon catalyst is hydrogenated at 1 atmosphere pressure. After about 3 hr (hydrogen uptake of 1 equivalent is absorbed), the reaction mixture is then filtered through diatomaceous earth, washed well with ethyl acetate, and concentrated under reduced pressure to yield 0.366 g of pure title product as a colorless oil. NMR absorptions are observed at 1.18, 1.2–2.43, 3.13–3.87, 3.87–4.33, 4.04, 4.68, and 5.10δ (deuterochloroform solvent). Infrared absorptions are observed at 3478, 1726, 1483, 1460, 1401, 1368, 1284, 1163, 1076, 1041, and 943 cm$^{-1}$.

EXAMPLE 2

4β-(trans-1′-octenyl)-5α-(2′-hydroxyethyl)-1,3-dioxane (formula XXXIV: Y$_1$ is trans—CH=CH—, M$_7$ and L$_1$ are α-H:β-H, and R$_7$ is n-butyl)

Refer to Chart B.

A. Chromium trioxide (4.18 g) is added in portions to 6.75 ml of pyridine and 70 ml of dichloromethane at 20° C. The mixture is then stirred for 2 hr under a argon atmosphere. To this stirred mixture is then added rapidly 1.05 g of the title product of Example 1 dissolved in 7 ml of dichloromethane. After about 25 min the entire reaction mixture is chromatographed on 100 g of silica gel, eluting with a mixture of 35% ethyl acetate in n-hexane. Accordingly, there is obtained the aldehyde corresponding to the formula XXXI primary alcohol.

As an alternative to the Collins oxidation of the preceeding paragraph, the aldehyde is produced employing a Moffatt reagent by dissolving the title compound of Example 1 (250 mg) in 5.0 ml of toluene and treating the resulting solution with 170 mg of dicyclohexylcarbodiimide in 1.5 ml of toluene, and 0.5 ml of 1 M phosphoric acid in dimethysulfoxide. After 120 min the reaction mixture is then treated with 302 mg of oxalic acid, dissolved in 0.60 ml of methanol. After evolution of carbon dioxide ceases, the reaction mixture is filtered and the filtrate chromatographed on (20 g of silica gel, eluting with ethyl acetate and n-hexane (1:4).

B. 4β-(3-oxo-trans-1-octenyl)-5α-(2′-hydroxyethyl)1,3-dioxane, 2′-pivalate.

From the product of Part A (425 mg) there is prepared a solution by dissolving this product in 20 ml of diethyl ether. The resulting solution is then treated with 4.8 ml of 0.5 M 2-oxo-heptylidine-tri-n-butyl phosphorane in diethyl ether. After 20 min, the reaction mixture is evaporated and the residue chromatographed on 80 g of silica gel. Eluting with ethyl acetate in n-hexane (1:1) fractions containing pure product are obtained.

Alternatively, a solution of 1.309 g of dimethyl 2-oxoheptylphosphonate and 30 ml of dry tetrahydrofuran is added with stirring to a cold solution of 0.60 g of potassium t-butoxide in 25 ml of dry tetrahydrofuran under a nitrogen atmosphere. After stirring at ambient temperature for 1.5 hr a portion of the reaction product from Part A is diluted with 7.0 ml of methylene chloride is added. After stirring at ambient temperature for 2 hr 0.35 ml of acetic acid is added and the resulting mixture is concentrated under reduced pressure, the residue diluted with ethyl acetate, and the resulting mixture washed with acidified (hydrochloric acid) brine, basified (sodium bicarbonate) brine, and then dried over magnesium sulfate and concentrated under reduced pressure. Chromatography of the residue yields the product of the preceeding paragraph.

C. 4β-(3-hydroxy-trans-1-octenyl)-5α-(2′-hydroxyethyl)-1,3-dioxane, 2′-pivalate (formula XXXII: R$_{12}$ is t-butyl, Y$_1$ is trans—CH=CH—, M$_1$ is a mixture of α-H:β-OH and α-OH:β-H, L$_1$ is α-H:β-H, and R$_7$ is n-butyl. To a mixture of 2.18 g of anhydrous zinc chloride and 15 ml of 1,2-dimethoxyethane under a nitrogen atmosphere is added with stirring 0.61 g of borohydride. The resulting mixture is then stirred at ambient temperature for 2 hr and thereafter cooled to −15° C. Thereafter a solution of 1.17 g of the reaction product of Part B and 10 ml of dimethoxyethane is added dropwise over 2 min. The resulting mixture is then stirred at −15° C. for 2 hr and thereafter at 0° C. for 1 hr. The resulting mixture is then cooled to 0° C. and 4.4 ml of water is added dropwise (hydrogen gas evolution). The resulting mixture is then diluted with 75 ml of ethyl acetate and filtered through diatamaceous earth. The filtrate is then washed with 30 ml of brine and the organic layer dried over magnesium sulfate and concentrated under reduced pressure. The resulting residue is then chromatographed on silica gel eluting with ethyl acetate in hexane and yielding the formula XXXII epimeric alcohol mixture.

Optionally these epimeric alcohols are separated by chromatography on silica gel eluting with methanol and chloroform.

D. 5α-(2′-hydroxyethyl)-4β-(3α- or 3β-t-butyldimethylsilyloxy-trans-1-octenyl)-1,3-dioxane, 2′-pivalate (formula XXXIII: R$_{12}$ is t-butyl, Y$_1$ is trans—CH=CH—, M$_7$ is α-t-butyldimethylsilyloxy:β-hydrogen or α-hydrogen:β-t-butyldimethylsilyloxy, L$_1$ is α-H:β-H, and R$_7$ is n-butyl). A solution of 0.5 g of the reaction product of Part C, 0.83 g of imidazole, and 0.92 g of t-butyldimethylchlorosilene in 2 ml of dry dimethylformamide is stirred at ambient temperature under a nitrogen atmosphere for 20 hr. The resulting solution is then cooled in an ice bath and 6 ml of water is added. After 30 min the mixture is then poured into cold brine and extracted with hexane. The organic extract is then washed with ice cold 2 N sodium bisulfate, ice cold saturated sodium bicarbonate, and brine and thereafter dried over sodium sulfate and concentrated to the formula XXXIII t-butyldimethylsilyl derivative. When the 3α-hydroxy reactant from Part C is employed, the corresponding 3α-t-butyldimethylsilyloxy product of formula XXXIII is obtained. Likewise, the 3β-hydroxy reactant yields the corresponding 3β-t-butyldimethylsilyl product.

E. 5α-(2′-hydroxyethyl)-4β-(trans-1-octenyl)-1,3-dioxane-2′-pivalate (formula XXXII or XXXIII: R$_{12}$ is t-butyl, Y$_1$ is trans—CH=CH—, M$_1$ or M$_7$ and L$_1$ are all α-H:β-H and R$_7$ is n-butyl). Methylamine (15 ml) is condensed and maintained at −30° C. to −40° C. while 0.94 g of the reaction product of Part D in 2 ml of a mixture of t-butanol and tetrahydrofuran (1:10) is added. Thereupon 3 small pieces of lithium metal (approximately ⅓ cm long) are added at a rate of one per minute. After 30 min from the time of lithium addition, 10 g of solid ammonium chloride are added and the methylamine is allowed to evaporate at ambient temperature under a stream of nitrogen. Thereafter ice cold 2 N aqueous sodium bisulfate is added and the resulting mixture extracted with 10% ethyl acetate in hexane. The combined organic extracts are then washed with brine, dried over sodium sulfate and concentrated yielding the formula XXXII or formula XXXIII product wherein $M_7$ is $\alpha$-H:$\beta$-H.

F. Title product is prepared from a solution of 1.0 g of the reaction product of Part E in 222 ml of methanol. This mixture is treated with 15 ml of 10% aqueous potassium hydroxide and after 48 hr the methanol is substantially evaporated under reduced pressure to a residue which is partitioned between hexane and ice cold 2 N sodium bisulfate and brine, dried over sodium sulfate and concentrated under reduced pressure to yield title product.

EXAMPLE 3

5$\alpha$-(2'-hydroxyethyl)-4$\beta$-(3$\alpha$- or 3$\beta$-t-butyldimethylsilyloxy-trans-1-octenyl)-1,3-dioxane (formula XXXIV: $Y_1$ is trans—CH=CH—, $M_7$ is $\alpha$-t-butyldimethylsilyloxy:$\beta$-hydrogen or $\alpha$-hydrogen:$\beta$-tbutyldimethylsilyloxy, $L_1$ is $\alpha$-H:$\beta$-H, and $R_7$ is n-butyl).

Refer to Chart B.

Following the procedure of Example 2, Part F, the reaction products of Example 2, Part D are transformed to the title product.

Following the procedure of Examples 2 and 3, and employing the appropriate Wittig reagent in Example 2, Part B, there are prepared each of the various formula XXXIV products of Chart B.

EXAMPLE 4

5-oxa-9,11,15-trideoxy-10-oxa-TXB$_1$, methyl ester (formula XLIII: $X_1$ is COOCH$_3$, g is one, $Y_1$ is trans—CH=CH—, $L_1$ and $M_1$ are $\alpha$-H:$\beta$-H, and $R_7$ is n-butyl).

Refer to Chart C.

A solution of potassium t-butoxide (1.77 g) in 30 ml of tetrahydrofuran is added at 0° C., with stirring, to a solution of the formula XXXIV title product of Example 2 in 30 ml of tetrahydrofuran. The resulting mixture is then stirred at 0° C. for 5 min and thereafter 5 ml of trimethyl ortho-4-bromobutyrate is added. Stirring is then continued at 0° C. for 2 hr and thereafter at about 25° C. for 16 hr. To this mixture is then added 30 ml of dimethylformamide and 0.5 g of potassium t-butoxide. The resulting mixture is then stirred for 20 hr. After solvent removal under reduced pressure, the residue is taken up with water and diethyl ether and dichloromethane (3:1). The organic phase is then washed with water and brine, dried, and concentrated to a residue. This residue is then dissolved in 6 ml of methanol at 0° C. and treated with 15 ml of cold water containing 2 drops of acetic acid. The resulting mixture is then stirred at 0° C. for 5 min, shaken with 200 ml of diethyl ether, 50 ml of dichloromethane, and 200 ml of brine. The organic phase is then washed with brine, dried, and concentrated under reduced pressure to yield a residue. Subjecting this residue to silica gel chromatography yields pure title product.

Following the procedure of Example 4, but employing the 3$\alpha$-t-butyldimethylsilyloxy or 3$\beta$-t-butyldimethylsilyloxy compounds of formula XXXIV, there is obtained the corresponding formula XLII t-butyldimethylsilyl ether. This formula XLII ether is then hydrolyzed to the formula XLIII 5-oxa-9,11-dideoxy-10-oxa-TXB$_1$, methyl ester, by dissolution in tetrahydrofuran followed by treatment with a solution of tetra-n-butyl ammonium fluoride in tetrahydrofuran at 65° C. for 2 hr, followed by cooling to 25° C. Product is obtained by concentration under reduced pressure, dilution with brine, and concentration with ethyl acetate, followed by washing the organic extracts with potassium bisulfate and brine, drying over magnesium sulfate and concentrating to a residue.

Employing each of the various formula XXXIV compounds described following Examples 2 and 3, there are prepared each of the various formula XLIII products wherein $X_1$ is —CO$_2$CH$_3$. The corresponding acid is obtained by saponification of the ester, i.e., see Example 2, Part F, and salts prepared therefrom by neutralization. Other esters, the corresponding primary alcohols, the various amides described above, and the various amines are all prepared by methods known in the art. Refer, for example, to the methodology described in U.S. Pat. Nos. 4,109,082, 4,112,224, 4,070,384, 4,073,808, 4,028,419, and 4,100,192, the relevant disclosures of which are incorporated here by reference.

EXAMPLE 5

4-Oxa-9,11,15-trideoxy-10-oxa-TXB$_1$, methyl ester (formula LV: $X_1$, g, $Y_1$, $M_1$, $L_1$, and $R_7$ are as defined in Example 4)

Refer to Chart D.

A. The title product of Example 2 is oxidized to the aldehyde corresponding to the formula LI primary alcohol by oxidation as described in Example 2, Part A.

B. 4$\beta$-(trans-1'-octenyl)-5$\alpha$-(3'-methoxy-cis-2'-propenyl)-1,3-dioxane (formula LII: $R_{26}$ is methyl, and $Y_1$, $M_1$, $L_1$, and $R_7$ are as defined in Example 4). A suspension of methoxymethyltriphenylphosphonium chloride (32.4 g) in 150 ml tetrahydrofuran is cooled to −15° C. To this suspension is added 69.4 ml of n-butyllithium in hexane (1.6 M) in 45 ml of tetrahydrofuran. After 30 min, the reaction product of Part A in 90 ml of tetrahydrofuran is added and the resulting mixture is stirred for 1.5 hr while warming to ambient temperature. The resulting solution is thereafter concentrated under reduced pressure and the residue partitioned between dichloromethane and water. The organic phase is dried and concentrated and the residue chromatographed on silica gel yielding the formula LII compound wherein $R_{26}$ is methyl.

C. 4$\beta$-(trans-1'-octenyl)-5$\alpha$-(3'-oxo-propyl)-1,3-dioxane (formula LIII: $Y_1$, $M_1$, $L_1$ and $R_7$ are as defined in Example 4).

The reaction product of Part B in 20 ml of tetrahydrofuran is treated with 50 ml of 66% aqueous acetic acid at about 55° C. for 2.5 hr. The resulting mixture is then concentrated under reduced pressure. Toluene is added to the residue and the solution is again concentrated and subjected to chromatography on silica gel eluting with chloroform and methanol (6:1), yielding the formula LIII product.

D. 4$\beta$-(trans-1'-octenyl)-5$\alpha$-(3'-hydroxypropyl)-1,3-dioxane (formula LIV: $Y_1$, $M_1$, $L_1$, and $R_7$ are as defined in Example 4).

A solution of the reaction product of Part C above in 20 ml of toluene is cooled to −78° C. and thereafter treated with 10 ml of 10% diisobutylaluminum hydride in toluene. The reaction mixture is stirred until TLC analysis indicates that the reduction to the alcohol is complete. Thereafter the cooling bath is removed and a mixture of tetrahydrofuran and water is slowly added. The reaction mixture is then stirred, allowed to warm to room temperature, and filtered through diatomacious earth. The filter cake is rinsed with toluene and the combined organic extracts are then dried over magnesium sulfate and concentrated to yield formula LIV product.

E. The title product is prepared from the formula LIV compound by treatment with trimethyl ortho-3-bromopropionate following the procedure of Example 4.

Employing the various alternative procedures described following Example 4, there are prepared from the formula LI compound each of the various formula LV products, including corresponding esters, salts, primary alcohols, amines, and amides.

EXAMPLE 6

4β-(trans-1'-octenyl)-5α-(2'-oxoethyl)-1,3-dioxane (formula XXXVI: $Y_1$ is trans—CH=CH—, $L_1$ and $M_1$ are α-H:β-H, and $R_7$ is n-butyl).

Refer to Chart B.

Following the procedure of Example 2, Part A, the title product of Example 2 is oxidized to the formula XXXVI compound.

EXAMPLE 7

4β-(3α- or 3β-hydroxy-trans-1-octenyl)-5α-(2'-oxoethyl)-1,3-dioxane (formula XXXVI: $Y_1$ is trans—CH=CH—, $L_1$ is α-hydrogen:β-hydrogen, $M_1$ is α-hydroxy:β-hydrogen or α-hydrogen:β-hydroxy, and $R_7$ is n-butyl).

Refer to Chart B.

A. 4β-(3α- or 3β-t-butyldimethylsilyloxy-trans-1'-octenyl)-5α-(2'-oxoethyl)-1,3-dioxane (formula XXXV: $Y_1$ is trans—CH=CH—, $M_1$ is α-trimethylsilyloxy:β-hydrogen or α-hydrogen:β-trimethylsilyloxy, $L_1$ is α-hydrogen:β-hydrogen, and $R_7$ is n-butyl).

Following the procedure of Example 2, Part A, the title product of Example 2 is transformed to the formula XXXV compound.

B. A solution of the reaction product of Part A in a mixture of acetic acid-water-tetrahydrofuran (20:10:3) is stirred at 25° C. for 18 hr under a nitrogen atmosphere. The resulting mixture is then poured into brine and extracted with ethyl acetate. The combined organic extracts are then washed with sodium bicarbonate solution and brine, dried over sodium sulfate, and concentrated under reduced pressure to yield crude formula XXXVI product. Chromatographing on silica gel yields pure formula XXXVI title compound.

EXAMPLE 8

9,11,15-trideoxy-10-oxa-TXB$_2$ (formula LXII: $X_1$ is —COOH, $R_2$ is hydrogen, g is one, n is one, $Y_1$ is trans—CH=CH—, $L_1$ and $M_1$ are α-H:β-H, and $R_7$ is n-butyl).

Refer to Chart E.

4-Carboxybutyltriphenylphosphonium bromide in benzene, 1.06 g, is added to a mixture of sodium hydride (0.208 g, 57% dispersion in oil) in 30 ml of dimethylsulfoxide. The resulting Wittig reagent is then combined with the title product of Example 6 (1 equivalent) in 20 ml of dimethylsulfoxide. The mixture is then stirred for 12 hr, diluted with 200 ml of toluene, and washed with potassium sulfate. The two lower layers are washed with dichloromethane and the organic phase is combined, and washed with brine, dried, and concentrated under reduced pressure. Chromatographing the residue on silica gel yields pure formula LXII product.

Following the procedure of Examples 6 and 7, there are prepared from the various formula XXXIV compounds described following Examples 2 and 3 each of the various formula LXI aldehydes, wherein n is one. The aldehydes thusly prepared are all transformed to the formula LXII compound wherein n is one by employing the appropriate Wittig reagent, e.g., 4-carboxybutyltriphenylphosphonium bromide, 5-carboxybromotriphenylphosphonium bromide, 6-carboxyboxyhexyltriphenylphosphonium bromide, or 4,4-difluoro-4-carboxybutyltriphenylphosphonium bromide.

Likewise, following the procedure of Example 8, but employing each of the various formula LXI compounds wherein n is 2, as described in Example 5, Part C, or otherwise prepared by the methods described in Example 5 from the appropriate formula LI starting material, there are prepared each of the various formula LXII carboxylic acids wherein n is 2 and p is zero.

EXAMPLE 9

9,11,15-trideoxy-10-oxa-TXB$_1$ (formula LXIII: $X_1$, $R_2$, g, $Y_1$, $L_1$, $M_1$, and $R_7$ are as defined in Example 8)

Refer to Chart E.

The title product of Example 8, a 5% rhodium-on-alumina catalyst, and ethyl acetate are stirred under 1 atmosphere of hydrogen at 0° C. until uptake of 1 equivalent of hydrogen is obtained. The resulting mixture is then filtered to remove catalyst and the filtrate concentrated under reduced pressure. The residue thusly obtained is chromatographed on silica gel and fractions containing pure formula LXIII product are obtained.

Following the procedure of Example 9, each of the various formula LXII compounds whose preparation is described above is transformed to the corresponding formula LXIII compound.

The various products described in and following Examples 8 and 9 are further transformed to corresponding esters, salts, amides, amines, or primary alcohols by methods hereinabove described.

EXAMPLE 10 trans-2,3-Didehydro-9,11,15-trideoxy-10-oxa-TXB$_1$, methyl ester (formula LXXXV: $X_1$ is —COOCH$_3$, g is one, $Y_1$ is trans—CH=CH—, $L_1$ and $M_1$ are α-H:β-H, and $R_7$ is n-butyl)

Refer to Chart G.

A. 2-Phenylselenidyl-9,11,15-trideoxy-10-oxa-TXB$_1$, methyl ester (formula LXXXII: $R_{12}$ is methyl and g, $Y_1$, $L_1$, $M_1$, and $R_7$ are as defined for the title compound).

A mixture of N-isopropylcyclohexylamine in 30 ml of tetrahydrofuran is cooled to −28° C. for 15 min and thereafter 2.4 g of 9,11,15-trideoxy-10-oxa-TXB$_1$, methyl ester in 20 ml of tetrahydrofuran is added. Thereafter 1.6 M n-butyllithium in hexane (4.7 ml) is added and the resulting mixture is stirred for 30 min. Thereupon diphenylselenide (1.76 g) in 15 ml of tetrahydrofuran is added at −78° C. Stirring is continued for an additional hour and the resulting mixture is then allowed to warm to 0° C., is poured into ammonium chloride (150 ml) and diethyl ether (150 ml), is extracted with diethyl ether, and the ethereal extracts washed with water and brine. After drying over sodium sulfate and concentrating under reduced pressure there is obtained crude formula LXXXII product.

B. 30% aqueous hydrogen peroxide (3.29 g) is added to the reaction product of Part A in 65 ml of methylene chloride at ambient temperature. Vigorous stirring is initiated for 1 hr, whereupon the layers are separated and the organic layer washed with 5% aqueous sodium bicarbonate, saturated sodium bicarbonate, and brine. The aqueous washings are then extracted with methylene chloride and the combined organic extracts are dried yielding crude title product. Chromatography on silica gel yields pure title product.

Following the procedure of Example 10, but employing each of the various $TXB_1$ compounds of formula LXXXI, there are obtained each of the various formula LXXXV trans-2,3-didehydro-carboxylic acids, esters, and salts. Further, as indicated above, such carboxylic acids, esters, and salts are transformed to corresponding amides, amines, and primary alcohols by methods known and described above.

Following the procedure of the above Examples, but employing appropriate starting material as described above, there are prepared 9,11-dideoxy-9,11,15-trideoxy-10-oxa-$TXB_2$ comounds, in free acid, ester, or amide form, or as corresponding 2-decarboxy-2-aminomethyl or 2-hydroxymethyl derivatives, which exhibit the following side chain variations:
15-methyl-;
16-methyl-;
16,16-dimethyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor-;
16-phenoxy-18,19,20-trinor-;
15-methyl-16-phenoxy-18,19,20-trinor-;
13,14-didehydro-;
15-methyl-13,14-didehydro-;
16-methyl-13,14-didehydro-;
16,16-dimethyl-13,14-didehydro-;
16-fluoro-13,14-didehydro-;
16,16-difluoro-13,14-didehydro-;
17-phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
13,14-dihydro-;
15-methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
15-methyl-16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
cis-13-;
15-methyl-cis-13-;
16-methyl-cis-13-;
16,16-dimethyl-cis-13-;
16-fluoro-cis-13-;
16,16-difluoro-cis-13-;
15-methyl-16,16-difluoro-cis-13-;
17-phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
15-methyl-17-phenyl-18,19,20-trinor-cis-13-;
16-methyl-17-phenyl-18,19,20-trinor-cis-13-;
16,16-dimethyl-17-phenyl-18,19,20-trinor-cis-13-;
16-fluoro-17-phenyl-18,19,20-trinor-cis-13-;
16,16-difluoro-17-phenyl-18,19,20-trinor-cis-13-;
15-methyl-16,16-difluoro-17-phenyl-18,19,20-trinor-cis-13-;
16-phenoxy-17,18,19,20-tetranor-cis-13-;
16-(m-trifluoromethylphenoxy)-17,18,19,20-tetranor-cis-13-;

16-(m-chlorophenoxy)-17,18,19,20-tetranor-cis-13-;
16-(p-fluorophenoxy)-17,18,19,20-tetranor-cis-13-;
15-methyl-16-phenoxy-17,18,19,20-tetranor-cis-13-;
16-phenoxy-18,19,20-trinor-cis-13-;
15-methyl-16-phenoxy-18,19,20-trinor-cis-13-;
16-methyl-16-phenoxy-18,19,20-trinor-cis-13-;
2,2-difluoro-;
2,2-difluoro-15-methyl-;
2,2-difluoro-16-methyl-;
2,2-difluoro-16,16-dimethyl-;
2,2,16-trifluoro-;
2,2,16,16-tetrafluoro-;
2,2,16,16-tetrafluoro-15-methyl-;
2,2-difluoro-17-phenyl-18,19,20-trinor-;
2,2-difluoro-15-methyl-17-phenyl-18,19,20-trinor-;
2,2-difluoro-17-(m-trifluoromethylphenyl)-18,19,20-trinor-;
2,2-difluoro-17-(m-chlorophenyl)-18,19,20-trinor-;
2,2-difluoro-17-(p-fluorophenyl)-18,19,20-trinor-;
2,2-difluoro-16-methyl-17-phenyl-18,19,20-trinor-;
2,2-difluoro-16,16-dimethyl-17-phenyl-18,19,20-trinor-;
2,2-difluoro-16-fluoro-17-phenyl-18,19,20-trinor-;
2,2-difluoro-16,16-difluoro-17-phenyl-18,19,20-trinor-;
2,2-difluoro-15-methyl-16,16-difluoro-17-phenyl-18,19,20-trinor-;
2,2-difluoro-16-phenoxy-17,18,19,20-tetranor-;
2,2-difluoro-16-(m-trifluoromethylphenoxy)-17,18,19,20-tetranor-;
2,2-difluoro-16-(m-chlorophenoxy)-17,18,19,20-tetranor-;
2,2-difluoro-16-(p-fluorophenoxy)-17,18,19,20-tetranor-;
2,2-difluoro-15-methyl-16-phenoxy-17,18,19,20-tetranor-;
2,2-difluoro-16-phenoxy-18,19,20-trinor-;
2,2-difluoro-15-methyl-16-phenoxy-18,19,20-trinor-;
2,2-difluoro-16-methyl-16-phenoxy-18,19,20-trinor-;
2,2-difluoro-16-methyl-13,14-didehydro-;
2,2-difluoro-16,16-dimethyl-13,14-didehydro-;
2,2-difluoro-16-fluoro-13,14-didehydro-;
2,2-difluoro-16,16-difluoro-13,14-didehydro-;
2,2,16,16-tetrafluoro-15-methyl-13,14-didehydro-;
2,2-difluoro-17-phenyl-18,19,20-trinor-13,14-didehydro-;
2,2-difluoro-17-(m-trifluoromethylphenyl)-18,19,20-trinor-13,14-didehydro-;
2,2-difluoro-17-(m-chlorophenyl)-18,19,20-trinor-13,14-didehydro-;
2,2-difluoro-17-(p-fluorophenyl)-18,19,20-trinor-13,14-didehydro-;
2,2-difluoro-15-methyl-17-phenyl-18,19,20-trinor-13,14-didehydro-;
2,2-difluoro-16-methyl-17-phenyl-18,19,20-trinor-13,14-didehydro-;
2,2-difluoro-16,16-dimethyl-17-phenyl-18,19,20-trinor-13,14-didehydro-;
2,2,16-trifluoro-17-phenyl-18,19,20-trinor-13,14-didehydro-;
2,2,16,16-tetrafluoro-17-phenyl-18,19,20-trinor-13,14-didehydro-;
2,2-difluoro-16-phenoxy-17,18,19,20-tetranor-13,14-didehydro-;
2,2-difluoro-16-(m-trifluoromethylphenoxy)-17,18,19,20-tetranor-13,14-didehydro-;
2,2-difluoro-16-(m-chlorophenoxy)-17,18,19,20-tetranor-13,14-didehydro-;
2,2-difluoro-15-methyl-16-phenoxy-17,18,19,20-tetranor-13,14-didehydro-;
2,2-difluoro-16-phenoxy-18,19,20-trinor-13,14-didehydro-;
2,2-difluoro-16-methyl-16-phenoxy-18,19,20-trinor-13,14-didehydro-;
2,2-difluoro-13,14-dihydro-;
2,2-difluoro-15-methyl-13,14-dihydro-;
2,2-difluoro-16-methyl-13,14-dihydro-;
2,2-difluoro-16,16-dimethyl-13,14-dihydro-;
2,2,16-trifluoro-13,14-dihydro-;
2,2,16,16-tetrafluoro-13,14-dihydro-;
2,2,16,16-tetrafluoro-15-methyl-13,14-dihydro-;
2,2-difluoro-17-phenyl-18,19,20-trinor-13,14-dihydro-;
2,2-difluoro-17-(m-trifluoromethylphenyl)-18,19,20-trinor-13,14-dihydro-;
2,2-difluoro-17-(m-chlorophenyl)-18,19,20-trinor-13,14-dihydro-;
2,2-difluoro-17-(p-fluorophenyl)-18,19,20-trinor-13,14-dihydro-;
2,2-difluoro-15-methyl-17-phenyl-18,19,20-trinor-13,14-dihydro-;
2,2-difluoro-16-methyl-17-phenyl-18,19,20-trinor-13,14-dihydro-;
2,2-difluoro-16,16-dimethyl-17-phenyl-18,19,20-trinor-13,14-dihydro-;
2,2,16-trifluoro-17-phenyl-18,19,20-dihydro-;
2,2,16,16-tetrafluoro-17-phenyl-18,19,20-dihydro-;
2,2-difluoro-16-phenoxy-17,18,19,20-tetranor-13,14-dihydro-;
2,2-difluoro-16-(m-trifluoromethylphenoxy)-17,18,19,20-tetranor-13,14-dihydro-;
2,2-difluoro-16-(m-chlorophenoxy)-17,18,19,20-tetranor-13,14-dihydro-;
2,2-difluoro-16-(p-fluorophenoxy)-17,18,19,20-tetranor-13,14-dihydro-;
2,2-difluoro-15-methyl-16-phenoxy-17,18,19,20-tetranor-13,14-dihydro-;
2,2-difluoro-16-phenoxy-18,19,20-trinor-13,14-dihydro-;
2,2-difluoro-15-methyl-16-phenoxy-18,19,20-trinor-13,14-dihydro-;
2,2-difluoro-16-methyl-16-phenoxy-18,19,20-trinor-13,14-dihydro-;
2,2-difluoro-cis-13-;
2,2-difluoro-15-methyl-cis-13-;
2,2-difluoro-16-methyl-cis-13-;
2,2-difluoro-16,16-dimethyl-cis-13-;
2,2,16-trifluoro-cis-13-;
2,2,16,16-tetrafluoro-cis-13-;
2,2,16,16-tetrafluoro-15-methyl-cis-13-;
2,2-difluoro-17-phenyl-18,19,20-trinor-cis-13-;
2,2-difluoro-17-(m-trifluoromethylphenyl)-18,19,20-trinor-cis-13-;
2,2-difluoro-17-(m-chlorophenyl)-18,19,20-trinor-cis-13-;
2,2-difluoro-17-(p-fluorophenyl)-18,19,20-trinor-cis-13-;
2,2-difluoro-15-methyl-17-phenyl-18,19,20-trinor-cis-13-;
2,2-difluoro-16-methyl-17-phenyl-18,19,20-trinor-cis-13-;
2,2-difluoro-16,16-dimethyl-17-phenyl-18,19,20-trinor-cis-13-;
2,2,16-trifluoro-17-phenyl-18,19,20-trinor-cis-13-;
2,2,16,16-tetrafluoro-17-phenyl-18,19,20-trinor-cis-13-;
2,2,16,16-tetrafluoro-17-phenyl-18,19,20-trinor-cis-13-;
2,2-difluoro-16-phenoxy-17,18,19,20-tetranor-cis-13-;
2,2-difluoro-16-(m-trifluoromethylphenoxy)-17,18,19,20-tetranor-cis-13-;

2,2-difluoro-16-(m-chlorophenoxy)-17,18,19,20-tetranor-cis-13-;
2,2-difluoro-16-(p-fluorophenoxy)-17,18,19,20-tetranor-cis-13-;
2,2-difluoro-15-methyl-16-phenoxy-17,18,19,20-tetranor-cis-13-;
2,2-difluoro-16-phenoxy-18,19,20-trinor-cis-13-;
2,2-difluoro-15-methyl-16-phenoxy-18,19,20-trinor-cis-13-;
2,2-difluoro-16-methyl-16-phenoxy-18,19,20-trinor-cis-13-;
2a,2b-dihomo-16-methyl-;
2a,2b-dihomo-16,16-dimethyl-;
2a,2b-dihomo-16-fluoro-;
2a,2b-dihomo-16,16-difluoro-;
2a,2b-dihomo-15-methyl-16,16-difluoro-;
2a,2b-dihomo-17-phenyl-18,19,20-trinor-;
2a,2b-dihomo-17-(m-trifluoromethylphenyl)-18,19,20-trinor-;
2a,2b-dihomo-17-(m-chlorophenyl)-18,19,20-trinor-;
2a,2b-dihomo-17-(p-fluorophenyl)-18,19,20-trinor-;
2a,2b-dihomo-15-methyl-17-phenyl-18,19,20-trinor-;
2a,2b-dihomo-16-methyl-17-phenyl-18,19,20-trinor-;
2a,2b-dihomo-16,16-dimethyl-17-phenyl-18,19,20-trinor-;
2a,2b-dihomo-16-fluoro-17-phenyl-18,19,20-trinor-;
2a,2b-dihomo-16,16-difluoro-17-phenyl-18,19,20-trinor-;
2a,2b-dihomo-15-methyl-16,16-difluoro-17-phenyl-18,19,20-trinor-;
2a,2b-dihomo-16-phenoxy-17,18,19,20-tetranor-;
2a,2b-dihomo-16-(m-trifluoromethylphenoxy)-17,18,19,20-tetranor-;
2a,2b-dihomo-16-(m-chlorophenoxy)-17,18,19,20-tetranor-;
2a,2b-dihomo-16-(p-fluorophenoxy)-17,18,19,20-tetranor-;
2a,2b-dihomo-15-methyl-16-phenoxy-17,18,19,20-tetranor-;
2a,2b-dihomo-16-phenoxy-18,19,20-trinor-;
2a,2b-dihomo-15-methyl-16-phenoxy-18,19,20-trinor-;
2a,2b-dihomo-16-methyl-16-phenoxy-18,19,20-trinor-;
2a,2b-dihomo-16-methyl-13,14-didehydro-;
2a,2b-dihomo-16,16-dimethyl-13,14-didehydro-;
2a,2b-dihomo-16-fluoro-13,14-didehydro-;
2a,2b-dihomo-16,16-difluoro-13,14-didehydro-;
2a,2b-dihomo-15-methyl-16,16-difluoro-13,14-didehydro-;
2a,2b-dihomo-17-phenyl-18,19,20-trinor-13,14-didehydro-;
2a,2b-dihomo-17-(m-trifluoromethylphenyl)-18,19,20-trinor-13,14-didehydro-;
2a,2b-dihomo-17-(m-chlorophenyl)-18,19,20-trinor-13,14-didehydro-;
2a,2b-dihomo-17-(p-fluorophenyl)-18,19,20-trinor-13,14-didehydro-;
2a,2b-dihomo-15-methyl-17-phenyl-18,19,20-trinor-13,14-didehydro-;
2a,2b-dihomo-16-methyl-17-phenyl-18,19,20-trinor-13,14-didehydro-;
2a,2b-dihomo-16,16-dimethyl-17-phenyl-18,19,20-trinor-13,14-didehydro-;
2a,2b-dihomo-16-fluoro-17-phenyl-18,19,20-trinor-13,14-didehydro-;
2a,2b-dihomo-16,16-difluoro-17-phenyl-18,19,20-trinor-13,14-didehydro-;
2a,2b-dihomo-16-phenoxy-17,18,19,20-tetranor-13,14-didehydro-;
2a,2b-dihomo-16-(m-trifluoromethylphenoxy)-17,18,19,20-tetranor-13,14-didehydro-;
2a,2b-dihomo-16-(m-chlorophenoxy)-17,18,19,20-tetranor-13,14-didehydro-;
2a,2b-dihomo-15-methyl-16-phenoxy-17,18,19,20-tetranor-;13,14-didehydro-;
2a,2b-dihomo-16-phenoxy-18,19,20-trinor-13,14-didehydro-;
2a,2b-dihomo-16-methyl-16-phenoxy-18,19,20-trinor-13,14-didehydro-;
2a,2b-dihomo-13,14-dihydro-;
2a,2b-dihomo-15-methyl-13,14-dihydro-;
2a,2b-dihomo-16-methyl-13,14-dihydro-;
2a,2b-dihomo-16,16-dimethyl-13,14-dihydro-;
2a,2b-dihomo-16-fluoro-13,14-dihydro-;
2a,2b-dihomo-16,16-difluoro-13,14-dihydro-;
16-methyl-2a,2b-dihomo-16,16-tetrafluoro-13,14-dihydro-;
2a,2b-dihomo-17-phenyl-18,19,20-trinor-13,14-dihydro-;
2a,2b-dihomo-17-(m-trifluoromethylphenyl)-18,19,20-trinor-13,14-dihydro-;
2a,2b-dihomo-17-(m-chlorophenyl)-18,19,20-trinor-13,14-dihydro-;
2a,2b-dihomo-17-(p-fluorophenyl)-18,19,20-trinor-13,14-dihydro-;
2a,2b-dihomo-15-methyl-17-phenyl-18,19,20-trinor-13,14-dihydro-;
2a,2b-dihomo-16-methyl-17-phenyl-18,19,20-trinor-13,14-dihydro-;
2a,2b-dihomo-16,16-dimethyl-17-phenyl-18,19,20-trinor-13,14-dihydro-;
2a,2b-dihomo-16-fluoro-17-phenyl-18,19,20-dihydro-;
2a,2b-dihomo-16,16-difluoro-17-phenyl-18,19,20-dihydro-;
2a,2b-dihomo-16-phenoxy-17,18,19,20-tetranor-13,14-dihydro-;
2a,2b-dihomo-16-(m-trifluoromethylphenoxy)-17,18,19,20-tetranor-13,14-dihydro-;
2a,2b-dihomo-16-(m-chlorophenoxy)-17,18,19,20-tetranor-13,14-dihydro-;
2a,2b-dihomo-16-(p-fluorophenoxy)-17,18,19,20-tetranor-13,14-dihydro-;
2a,2b-dihomo-15-methyl-16-phenoxy-17,18,19,20-tetranor-13,14-dihydro-;
2a,2b-dihomo-16-phenoxy-18,19,20-trinor-13,14-dihyro-;
2a,2b-dihomo-15-methyl-16-phenoxy-18,19,20-trinor-13,14-dihydro-;
2a,2b-dihomo-16-methyl-16-phenoxy-18,19,20-trinor-13,14-dihydro-;
2a,2b-dihomo-cis-13-;
2a,2b-dihomo-15-methyl-cis-13-;
2a,2b-dihomo-16-methyl-cis-13-;
2a,2b-dihomo-16,16-dimethyl-cis-13-;
2a,2b-dihomo-16-fluoro-cis-13-;
2a,2b-dihomo-16,16-difluoro-cis-13-;
2a,2b-dihomo-15-methyl-16,16-difluoro-cis-13-;
2a,2b-dihomo-17-phenyl-18,19,20-trinor-cis-13-;
2a,2b-dihomo-17-(m-trifluoromethylphenyl)-18,19,20-trinor-cis-13-;
2a,2b-dihomo-17-(m-chlorophenyl)-18,19,20-trinor-cis-13-;
2a,2b-dihomo-17-(p-fluorophenyl)-18,19,20-trinor-cis-13-;
2a,2b-dihomo-15-methyl-17-phenyl-18,19,20-trinor-cis-13-;

2a,2b-dihomo-16-methyl-17-phenyl-18,19,20-trinor-cis-13-;
2a,2b-dihomo-16,16-dimethyl-17-phenyl-18,19,20-trinor-cis-13-;
2a,2b-dihomo-16-fluoro-17-phenyl-18,19,20-trinor-cis-13-;
2a,2b-dihomo-16,16-difluoro-17-phenyl-18,19,20-trinor-cis-13-;
2a,2b-dihomo-15-methyl-16,16-difluoro-17-phenyl-18,19,20-trinor-cis-13-;
2a,2b-dihomo-16-phenoxy-17,18,19,20-tetranor-cis-13-;
2a.2b-dihomo-16-(m-trifluoromethylphenoxy)-17,18,19,20-tetranor-cis-13-;
2a,2b-dihomo-16-(m-chlorophenoxy)-17,18,19,20-tetranor-cis-13-;
2a.2b-dihomo-16-(p-fluorophenoxy)-17,18,19,20-tetranor-cis-13-;
2a,2b-dihomo-15-methyl-16-phenoxy-17,18,19,20-tetranor-cis-13-;
2a,2b-dihomo-16-phenoxy-18,19,20-trinor-cis-13-;
2a,2b-dihomo-15-methyl-16-phenoxy-18,19,20-trinor-cis-13-;
2a,2b-dihomo-16-methyl-16-phenoxy-18,19,20-trinor-cis-13-;

Following the procedure of the above Examples, but employing apropriate starting material as described above there are prepared 9,11-dideoxy- or 9,11,15-trideoxy-10-oxa-TXB$_1$ compounds, in free acid or methyl ester form or as 2-decarboxy-2-aminomethyl or 2-hydroxymethyl derivatives which exhibit the following side chain characteristics:
15-methyl-;
16-methyl-;
16,16-dimethyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor-;
16-phenoxy-18,19,20-trinor-;
15-methyl-16-phenoxy-18,19,20-trinor-;
13,14-didehydro-;
15-methyl-13,14-didehydro-;
16-methyl-13,14-didehydro-;
16,16-dimethyl-13,14-didehydro-;
16-fluoro-13,14-didehydro-;
16,16-difluoro-13,14-didehydro-;
17-phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro;
16-(m-trifluoromethylphenoxy)-17,18,19,20-tetranor-13,14-didehydro-;
16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
13,14-dihydro-;
15-methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
15-methyl-16,16-difluoro-17-phenyl-18,19,20-trinor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
cis-13-;
15-methyl-cis-13-;
16-methyl-cis-13-;
16,16-dimethyl-cis-13-;
16-fluoro-cis-13-;
16,16-difluoro-cis-13-;
15-methyl-16,16-difluoro-cis-13-;
17-phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
15-methyl-17-phenyl-18,19,20-trinor-cis-13-;
16-methyl-17-phenyl-18,19,20-trinor-cis-13-;
16,16-dimethyl-17-phenyl-18,19,20-trinor-cis-13-;
16-fluoro-17-phenyl-18,19,20-trinor-cis-13-;
16,16-difluoro-17-phenyl-18,19,20-trinor-cis-13-;
15-methyl-16,16-difluoro-17-phenyl-18,19,20-trinor-cis-13-;
16-phenoxy-17,18,19,20-tetranor-cis-13-;

16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
15-methyl-16-phenoxy-17,18,19,20-tetranor-cis-13-;
16-phenoxy-18,19,20-trinor-cis-13-;
15-methyl-16-phenoxy-18,19,20-trinor-cis-13-;
16-methyl-16-phenoxy-18,19,20-trinor-cis-13-;
2,2-difluoro-;
15-methyl-2,2-difluoro-;
2,2-difluoro-16-methyl-;
2,2-difluoro-16,16-dimethyl-;
2,2,16-trifluoro-;
2,2,16,16-tetrafluoro-;
2,2,16,16-tetrafluoro-15-methyl-;
2,2-difluoro-17-phenyl-18,19,20-trinor-;
2,2-difluoro-15-methyl-17-phenyl-18,19,20-trinor-;
2,2-difluoro-17-(m-trifluoromethylphenyl)-18,19,20-trinor-;
2,2-difluoro-17-(m-chlorophenyl)-18,19,20-trinor-;
2,2-difluoro-17-(p-fluorophenyl)-18,19,20-trinor;
2,2-difluoro-16-methyl-17-phenyl-18,19,20-trinor-;
2,2-difluoro-16,16-dimethyl-17-phenyl-18,19,20-trinor-;
2,2,16-trifluoro-17-phenyl-18,19,20-trinor-;
2,2,16,16-tetrafluoro-17-phenyl-18,19,20-trinor-;
2,2,16,16-tetrafluoro-15-methyl-17-phenyl-18,19,20-trinor-;
2,2-difluoro-16-phenoxy-17,18,19,20-tetranor-;
2,2-difluoro-16-(m-trifluoromethylphenoxy)-17,18,19,20-tetranor-;
2,2-difluoro-16-(m-chlorophenoxy)-17,18,19,20-tetranor-;
2,2-difluoro-16-(p-fluorophenoxy)-17,18,19,20-tetranor-;
2,2-difluoro-15-methyl-16-phenoxy-17,18,19,20-tetranor-;
2,2-difluoro-16-phenoxy-18,19,20-trinor-;
2,2-difluoro-15-methyl-16-phenoxy-18,19,20-trinor-;
2,2-difluoro-16-methyl-16-phenoxy-18,19,20-trinor-;
2,2-difluoro-16-methyl-13,14-didehydro-;
2,2-difluoro-16,16-dimethyl-13,14-didehydro-;
2,2,16-trifluoro-13,14-didehydro-;
2,2,16,16-tetrafluoro-13,14-didehydro-;
2,2,16,16-tetrafluoro-15-methyl-13,14-didehydro-;
2,2-difluoro-17-phenyl-18,19,20-trinor-13,14-didehydro-;
2,2-difluoro-17-(m-trifluoromethylphenyl)-18,19,20-trinor-13,14-didehydro-;
2,2-difluoro-17-(m-chlorophenyl)-18,19,20-trinor-13,14-didehydro-;
2,2-difluoro-17-(p-fluorophenyl)-18,19,20-trinor-13,14-didehydro-;
2,2-difluoro-15-methyl-17-phenyl-18,19,20-trinor-13,14-didehydro-;
2,2-difluoro-16-methyl-17-phenyl-18,19,20-trinor-13,14-didehydro-;
2,2-difluoro-16,16-dimethyl-17-phenyl-18,19,20-trinor-13,14-didehydro-;
2,2,16-trifluoro-17-phenyl-18,19,20-trinor-13,14-didehydro-;
2,2,16,16-tetrafluoro-17-phenyl-18,19,20-trinor-13,14-didehydro-;
2,2-difluoro-16-phenoxy-17,18,19,20-tetranor-13,14-didehydro-;
2,2-difluoro-16-(m-trifluoromethylphenoxy)-17,18,19,20-tetranor-13,14-didehydro-;
2,2-difluoro-16-(m-chlorophenoxy)-17,18,19,20-tetranor-13,14-didehydro-;
2,2-difluoro-15-methyl-16-phenoxy-17,18,19,20-tetranor-; 13,14-didehydro-;
2,2-difluoro-16-phenoxy-18,19,20-trinor-13,14-didehydro-;
2,2-difluoro-16-methyl-16-phenoxy-18,19,20-trinor-13,14-didehydro-;
2,2-difluoro-13,14-dihydro-;
2,2-difluoro-15-methyl-13,14-dihydro-;
2,2-difluoro-16-methyl-13,14-dihydro-;
2,2-difluoro-16,16-dimethyl-13,14-dihydro-;
2,2,16-trifluoro-13,14-dihydro-;
2,2,16,16-tetrafluoro-13,14-dihydro-;
16-methyl-2,2,16,16-tetrafluoro-13,14-dihydro-;
2,2-difluoro-17-phenyl-18,19,20-trinor-13,14-dihydro-;
2,2-difluoro-17-(m-trifluoromethylphenyl)-18,19,20-trinor-13,14-dihydro-;
2,2-difluoro-17-(m-chlorophenyl)-18,19,20-trinor-13,14-dihydro-;
2,2-difluoro-17-(p-fluorophenyl)-18,19,20-trinor-13,14-dihydro-;
2,2-difluoro-15-methyl-17-phenyl-18,19,20-trinor-13,14-dihydro-;
2,2-difluoro-15-methyl-17-(p-fluorophenyl)-18,19,20-trinor-13,14-dihydro-;
2,2-difluoro-16-methyl-17-phenyl-18,19,20-trinor-13,14-dihydro-;
2,2-difluoro-16,16-dimethyl-17-phenyl-18,19,20-trinor-13,14-dihydro-;
2,2,16-trifluoro-17-phenyl-18,19,20-dihydro-;
2,2,16,16-tetrafluoro-17-phenyl-18,19,20-dihydro-;
2,2-difluoro-16-phenoxy-17,18,19,20-tetranor-13,14-dihydro-;
2,2-difluoro-16-(m-trifluoromethylphenoxy)-17,18,19,20-tetranor-13,14-dihydro-;
2,2-difluoro-16-(m-chlorophenoxy)-17,18,19,20-tetranor-13,14-dihydro-;
2,2-difluoro-16-(p-fluorophenoxy)-17,18,19,20-tetranor-13,14-dihydro-;
2,2-difluoro-15-methyl-16-phenoxy-17,18,19,20-tetranor-13,14-dihydro-;
2,2-difluoro-16-phenoxy-18,19,20-trinor-13,14-dihydro-;
2,2-difluoro-15-methyl-16-phenoxy-18,19,20-trinor-13,14-dihydro-;
2,2-difluoro-16-methyl-16-phenoxy-18,19,20-trinor-13,14-dihydro-;
2,2-difluoro-cis-13-;
15-methyl-2,2-difluoro-cis-13-;
2,2-difluoro-16-methyl-cis-13-;
2,2-difluoro-16,16-dimethyl-cis-13-;
2,2,16-trifluoro-cis-13-;
2,2,16,16-tetrafluoro-cis-13-;
2,2,16,16-tetrafluoro-15-methyl-cis-13-;
2,2-difluoro-17-phenyl-18,19,20-trinor-cis-13-;
2,2-difluoro-17-(m-trifluoromethylphenyl)-18,19,20-trinor-cis-13-;
2,2-difluoro-17-(m-chlorophenyl)-18,19,20-trinor-cis-13-;
2,2-difluoro-17-(p-fluorophenyl)-18,19,20-trinor-cis-13-;
2,2-difluoro-15-methyl-17-phenyl-18,19,20-trinor-cis-13-;
2,2-difluoro-16-methyl-17-phenyl-18,19,20-trinor-cis-13-;
2,2-difluoro-16,16-dimethyl-17-phenyl-18,19,20-trinor-cis-13-;
2,2,16-trifluoro-17-phenyl-18,19,20-trinor-cis-13-;
2,2,16,16-tetrafluoro-17-phenyl-18,19,20-trinor-cis-13-;

2,2,16,16-tetrafluoro-15-methyl-17-phenyl-18,19,20-trinor-cis-13-;
2,2-difluoro-16-phenoxy-17,18,19,20-tetranor-cis-13-;
2,2-difluoro-15-methyl-16-phenoxy-17,18,19,20-tetranor-cis-13-;
2,2-difluoro-16-(m-trifluoromethylphenoxy)-17,18,19,20-tetranor-cis-13-;
2,2-difluoro-16-(m-chlorophenoxy)-17,18,19,20-tetranor-cis-13-;
2,2-difluoro-16-(p-fluorophenoxy)-17,18,19,20-tetranor-cis-13-;
2,2-difluoro-16-phenoxy-18,19,20-trinor-cis-13-;
2,2-difluoro-15-methyl-16-phenoxy-18,19,20-trinor-cis-13-;
2,2-difluoro-16-methyl-16-phenoxy-18,19,20-trinor-cis-13-;
2a,2b-dihomo-;
2a,2b-dihomo-15-methyl-;
2a,2b-dihomo-16-methyl-;
2a,2b-dihomo-16,16-dimethyl-;
2a,2b-dihomo-16-fluoro-;
2a,2b-dihomo-16,16-difluoro-;
2a,2b-dihomo-15-methyl-16,16-difluoro-;
2a,2b-dihomo-17-phenyl-18,19,20-trinor-;
2a,2b-dihomo-17-(m-trifluoromethylphenyl)-18,19,20-trinor-;
2a,2b-dihomo-17-(m-chlorophenyl)-18,19,20-trinor-;
b 2a,2b-dihomo-17-(p-fluorophenyl)-18,19,20-trinor-;
2a,2b-dihomo-15-methyl-17-phenyl-18,19,20-trinor-;
2a,2b-dihomo-16-methyl-17-phenyl-18,19,20-trinor-;
2a,2b-dihomo-16,16-dimethyl-17-phenyl-18,19,20-trinor-;
2a,2b-dihomo-16-fluoro-17-phenyl-18,19,20-trinor-;
2a,2b-dihomo-16,16-difluoro-17-phenyl-18,19,20-trinor-;
2a,2b-dihomo-15-methyl-16,16-difluoro-17-phenyl-18,19,20-trinor-;
2a,2b-dihomo-16-phenoxy-17,18,19,20-tetranor-;
2a,2b-dihomo-16-(m-trifluoromethylphenoxy)-17,18,19,20-tetranor-;
2a,2b-dihomo-16-(m-chlorophenoxy)-17,18,19,20-tetranor-;
2a,2b-dihomo-16-(p-fluorophenoxy)17,18,19,20-tetranor-;
2a,2b-dihomo-15-methyl-16-phenoxy-17,18,19,20-tetranor-;
2a,2b-dihomo-16-phenoxy-18,19,20-trinor-;
2a,2b-dihomo-15-methyl-16-phenoxy-18,19,20-trinor-;
2a,2b-dihomo-16-methyl-16-phenoxy-18,19,20-trinor-;
2a,2b-dihomo-16-methyl-13,14-didehydro-;
2a,2b-dihomo-16,16-dimethyl-13,14-didehydro-;
2a,2b-dihomo-16-fluoro-13,14-didehydro-;
2a,2b-dihomo-16,16-difluoro-13,14-didehydro-;
2a,2b-dihomo-15-methyl-16,16-difluoro-13,14-didehydro-;
2a,2b-dihomo-17-phenyl-18,19,20-trinor-13,14-didehydro-;
2a,2b-dihomo-17-(m-trifluoromethylphenyl)-18,19,20-trinor-13,14-didehydro-;
2a,2b-dihomo-17-(m-chlorophenyl)-18,19,20-trinor-13,14-didehydro-;
2a,2b-dihomo-17-(p-fluorophenyl)-18,19,20-trinor-13,14-didehydro-;
2a,2b-dihomo-15-methyl-17-phenyl-18,19,20-trinor-13,14-didehydro-;
2a,2b-dihomo-16-methyl-17-phenyl-18,19,20-trinor-13,14-didehydro-;
2a,2b-dihomo-16,16-dimethyl-17-phenyl-18,19,20-trinor-13,14-didehydro-;
2a,2b-dihomo-16-fluoro-17-phenyl-18,19,20-trinor-13,14-didehydro-;
2a,2b-dihomo-16,16-difluoro-17-phenyl-18,19,20-trinor-13,14-dihydro-;
2a,2b-dihomo-16-phenoxy-17,18,19,20-tetranor-13,14-didehydro-;
2a,2b-dihomo-16-(m-trifluoromethylphenoxy)-17,18,19,20-tetranor-13,14-didehydro-;
2a,2b-dihomo-16-(m-chlorophenoxy)-17,18,19,20-tetranor-13,14-didehydro-;
2a,2b-dihomo-15-methyl-16-phenoxy-17,18,19,20-tetranor-; 13,14-didehydro-;
2a,2b-dihomo-16-phenoxy-18,19,20-trinor-13,14-didehydro-;
2a,2b-dihomo-16-methyl-16-phenoxy-18,19,20-trinor-13,14-didehydro-;
2a,2b-dihomo-13,14-dihydro-;
2a,2b-dihomo-15-methyl-12,14-dihydro-;
2a,2b-dihomo-16-methyl-13,14-dihydro-;
2a,2b-dihomo-16,16-dimethyl-13,14-dihydro-;
2a,2b-dihomo-16-fluoro-13,14-dihydro-;
2a,2b-dihomo-16,16-difluoro-13,14-dihydro-;
15-methyl-2a,2b-dihomo-16,16-difluoro-13,14-dihydro-;
2a,2b-dihomo-17-phenyl-18,19,20-trinor-13,14-dihydro-;
2a,2b-dihomo-17-(m-trifluoromethylphenyl)-18,19,20-trinor-13,14-dihydro-;
2a,2b-dihomo-17-(m-chlorophenyl)-18,19,20-trinor-13,14-dihydro-;
2a,2b-dihomo-17-(p-fluorophenyl)-18,19,20-trinor-13,14-dihydro-;
2a,2b-dihomo-15-methyl-17-(p-fluorophnyl)-18,19,20-trinor-13,14-dihydro-;
2a,2b-dihomo-15-methyl-17-phenyl-18,19,20-trinor-13,14-dihydro-;
2a,2b-dihomo-16-methyl-17-phenyl-18,19,20-trinor-13,14-dihydro-;
2a,2b-dihomo-16,16-dimethyl-17-phenyl-18,19,20-trinor-13,14-dihydro-;
2a,2b-dihomo-16-fluoro-17-phenyl-18,19,20-dihydro-;
2a,2b-dihomo-16,16-difluoro-17-phenyl-18,19,20-dihydro-;
2a,2b-dihomo-16-phenoxy-17,18,19,20-tetranor-13,14-dihydro-;
2a,2b-dihomo-16-(m-trifluoromethylphenoxy)-17,18,19,20-tetranor-13,14-dihydro-;
2a,2b-dihomo-16-(m-chlorophenoxy)-17,18,19,20-tetranor-13,14-dihydro-;
2a,2b-dihomo-16-(p-fluorophenoxy)-17,18,19,20-tetranor-13,14-dihydro-;
2a,2b-dihomo-15-methyl-16-phenoxy-17,18,19,20-tetranor-13,14-dihydro-;
2a,2b-dihomo-16-phenoxy-18,19,20-trinor-13,14-dihydro-;
2a,2b-dihomo-15-methyl-16-phenoxy-18,19,20-trinor-13,14-dihydro-;
2a,2b-dihomo-16-methyl-16-phenoxy-18,19,20-trinor-13,14-dihydro-;
2a,2b-dihomo-cis-13-;
2a,2b-dihomo-15-methyl-cis-13-;
2a,2b-dihomo-16-methyl-cis-13-;
2a,2b-dihomo-16,16-dimethyl-cis-13-;
2a,2b-dihomo-16-fluoro-cis-13-;
2a,2b-dihomo-16,16-difluoro-cis-13-;
2a,2b-dihomo-15-methyl-16,16-difluoro-cis-13-;
2a,2b-dihomo-17-phenyl-18,19,20-trinor-cis-13-;

2a,2b-dihomo-17-(m-trifluoromethylphenyl)-18,19,20-trinor-cis-13-;
2a,2b-dihomo-17-(m-chlorophenyl)-18,19,20-trinor-cis-13-;
2a,2b-dihomo-17-(p-fluorophenyl)-18,19,20-trinor-cis-13-;
2a,2b-dihomo-15-methyl-17-phenyl-18,19,20-trinor-cis-13-;
2a,2b-dihomo-16-methyl-17-phenyl-18,19,20-trinor-cis-13-;
2a,2b-dihomo-16,16-dimethyl-17-phenyl-18,19,20-trinor-cis-13-;
2a,2b-dihomo-16-fluoro-17-phenyl-18,19,20-trinor-cis-13-;
2a,2b-dihomo-16,16-difluoro-17-phenyl-18,19,20-trinor-cis-13-;
2a,2b-dihomo-15-methyl-16,16-difluoro-17-phenyl-18,19,20-trinor-cis-13-;
2a,2b-dihomo-16-phenoxy-17,18,19,20-tetranor-cis-13-;
2a.2b-dihomo-16-(m-trifluoromethylphenoxy)-17,18,19,20-tetranor-cis-13-;
2a,2b-dihomo-16-(m-chlorophenoxy)-17,18,19,20-tetranor-cis-13-;
2a.2b-dihomo-16-(p-fluorophenoxy)-17,18,19,20-tetranor-cis-13-;
2a,2b-dihomo-15-methyl-16-phenoxy-17,18,19,20-tetranor-cis-13-;
2a,2b-dihomo-16-phenoxy-18,19,20-trinor-cis-13-;
2a,2b-dihomo-15-methyl-16-phenoxy-18,19,20-trinor-cis-13-;
2a,2b-dihomo-16-methyl-16-phenoxy-18,19,20-trinor-cis-13-;
cis-4,5-didehydro-;
cis-4,5-didehydro-15-methyl-;
cis-4,5-didehydro-16-methyl-;
cis-4,5-didehydro-16,16-dimethyl-;
cis-4,5-didehydro-16-fluoro-;
cis-4,5-didehydro-16,16-difluoro-;
cis-4,5-didehydro-15-methyl-16,16-difluoro-;
cis-4,5-didehydro-17-phenyl-18,19,20-trinor-;
cis-4,5-didehydro-17-(m-trifluoromethylphenyl)-18,19,20-trinor-;
cis-4,5-didehydro-17-(m-chlorophenyl)-18,19,20-trinor-;
cis-4,5-didehydro-17-(p-fluorophenyl)-18,19,20-trinor-;
cis-4,5-didehydro-15-methyl-17-phenyl-18,19,20-trinor-;
cis-4,5-didehydro-16-methyl-17-phenyl-18,19,20-trinor-;
cis-4,5-didehydro-16,16-dimethyl-17-phenyl-18,19,20-trinor-;
cis-4,5-didehydro-16-fluoro-17-phenyl-18,19,20-trinor-;
cis-4,5-didehydro-16,16-difluoro-17-phenyl-18,19,20-trinor-;
cis-4,5-didehydro-15-methyl-16,16-difluoro-17-phenyl-18,19,20-trinor-;
cis-4,5-didehydro-16-phenoxy-17,18,19,20-tetranor-;
cis-4,5-didehydro-16-(m-trifluoromethylphenoxy)-17,18,19,20-tetranor-;
cis-4,5-didehydro-16-(m-chlorophenoxy)-17,18,19,20-tetranor-;
cis-4,5-didehydro-16-(p-fluorophenoxy)-17,18,19,20-tetranor-;
cis-4,5-didehydro-15-methyl-16-phenoxy-17,18,19,20-tetranor-;
cis-4,5-didehydro-16-phenoxy-18,19,20-trinor-;
cis-4,5-didehydro-15-methyl-16-phenoxy-18,19,20-trinor-;
cis-4,5-didehydro-16-methyl-16-phenoxy-18,19,20-trinor-;
cis-4,5-didehydro-16-methyl-13,14-didehydro-;
cis-4,5-didehydro-16,16-dimethyl-13,14-didehydro-;
cis-4,5-didehydro-16-fluoro-13,14-didehydro-;
cis-4,5didehydro-16,16-difluoro-13,14-didehydro-;
cis-4,5-didehydro-15-methyl-16,16-difluoro-13,14-didehydro-;
cis-4,5-didehydro-17-phenyl-18,19,20-trinor-13,14-didehydro-;
cis-4,5-didehydro-17-(m-trifluoromethylphenyl)-18,19,20-trinor-13,14-didehydro-;
cis-4,5-didehydro-17-(m-chlorophenyl)-18,19,20-trinor-13,14-didehydro-;
cis-4,5-didehydro-17-(p-fluorophenyl)-18,19,20-trinor-13,14-didehydro-;
cis-4,5-didehydro-15-methyl-17-phenyl-18,19,20-trinor-13,14-didehydro-;
cis-4,5-didehydro-16-methyl-17-phenyl-18,19,20-trinor-13,14-didehydro;
cis-4,5-didehydro-16,16-dimethyl-17-phenyl-18,19,20-trinor-13,14-didehydro-;
cis-4,5-didehydro-16-fluoro-17-phenyl-18,19,20-trinor-13,14-didehydro-;
cis-4,5-didehydro-16,16-difluoro-17-phenyl-18,19,20-trinor-13,14-dihydro-;
cis-4,5-didehydro-16-phenoxy-17,18,19,20-tetranor-13,14-didehydro-;
cis-4,5-didehydro-16-(m-trifluoromethylphenoxy)-17,18,19,20-tetranor-13,14-didehydro-;
cis-4,5-didehydro-16-(m-chlorophenoxy)-17,18,19,20-tetranor-13,14-didehydro-;
cis-4,5-didehydro-15-methyl-16-phenoxy-17,18,19,20-tetranor-13,14-didehydro-;
cis-4,5-didehydro-16-phenoxy-18,19,20-trinor-13,14-didehydro-;
cis-4,5-didehydro-16-methyl-16-phenoxy-18,19,20-trinor-13,14-didehydro-;
cis-4,5-didehydro-13,14-dihydro-;
cis-4,5-didehydro-15-methyl-13,14-dihydro-;
cis-4,5-didehydro-16-methyl-13,14-dihydro-;
cis-4,5-didehydro-16,16-dimethyl-13,14-dihydro-;
cis-4,5-didehydro-16-fluoro-13,14-dihydro-;
cis-4,5-didehydro-16,16-difluoro-13,14-dihydro-;
cis-4,5-didehydro-15-methyl-16,16-difluoro-13,14-didehydro-;
cis-4,5-didehydro-17-phenyl-18,19,20-trinor-13,14-didehydro-;
cis-4,5-didehydro-17-(m-trifluoromethylphenyl)-18,19,20-trinor-13,14-dihydro-;
cis-4,5-didehydro-17-(m-chlorophenyl)-18,19,20-trinor-13,14-dihydro-;
cis-4,5-didehydro-17-(p-fluorophenyl)-18,19,20-trinor-13,14-dihydro-;
cis-4,5-didehydro-15-methyl-17-(p-fluorophenyl)-18,19,20-trinor-13,14-dihydro-;
cis-4,5-didehydro-15-methyl-17-phenyl-18,19,20-trinor-13,14-dihydro-;
cis-4,5-didehydro-16-methyl-17-phenyl-18,19,20-trinor-13,14-dihydro-;
cis-4,5-didehydro-16,16-dimethyl-17-phenyl-18,19,20-trinor-13,14-dihydro-;
cis-4,5-didehydro-16-fluoro-17-phenyl-18,19,20-dihydro-;
cis-4,5-didehydro-16,16-difluoro-17-phenyl-18,19,20-trinor-dihydro-;
cis-4,5-didehydro-16-phenoxy-17,18,19,20-tetranor-13,14-dihydro-;

cis-4,5-didehydro-16-(m-trifluoromethylphenoxy)-17,18,19,20-tetranor-13,14-dihydro-;
cis-4,5-didehydro-16-(m-chlorophenoxy)-17,18,19,20-tetranor-13,14-dihydro-;
cis-4,5-didehydro-16-(p-fluorophenoxy)-17,18,19,20-tetranor-13,14-dihydro-;
cis-4,5-didehydro-15-methyl-16-phenoxy-17,18,19,20-tetranor-13,14-dihydro-;
cis-4,5-didehydro-16-phenoxy-18,19,20-trinor-13,14-didehydro-;
cis-4,5-didehydro-15-methyl-16-phenoxy-18,19,20-trinor-13,14-dihydro-;
cis-4,5-didehydro-16-methyl-16-phenoxy-18,19,20-trinor-13,14-dihydro-;
cis-4,5-didehydro-cis-13-;
cis-4,5-didehydro-15-methyl-cis-13-;
cis-4,5-didehydro-16-methyl-cis-13-;
cis-4,5-didehydro-16,16-dimethyl-cis-13-;
cis-4,5-didehydro-16-fluoro-cis-13-;
cis-4,5-didehydro-16,16-difluoro-cis-13-;
cis-4,5-didehydro-15-methyl-16,16-difluoro-cis-13-;
cis-4,5-didehydro-17-phenyl-18,19,20-trinor-cis-13-;
cis-4,5-didehydro-17-(m-trifluoromethylphenyl)-18,19,20-trinor-cis-13-;
cis-4,5-didehydro-17-(m-chlorophenyl)-18,19,20-trinor-cis-13-;
cis-4,5-didehydro-17-(p-fluorophenyl)-18,19,20-trinor-cis-13-;
cis-4,5-didehydro-15-methyl-17-phenyl-18,19,20-trinor-cis-13-;
cis-4,5-didehydro-16-methyl-17-phenyl-18,19,20-trinor-cis-13-;
cis-4,5-didehydro-16,16-dimethyl-17-phenyl-18,19,20-trinor-cis-13-;
cis-4,5-didehydro-16-fluoro-17-phenyl-18,19,20-trinor-cis-13-;
cis-4,5-didehydro-16,16-difluoro-17-phenyl-18,19,20-trinor-cis-13-;
cis-4,5-didehydro-15-methyl-16,16-difluoro-17-phenyl-18,19,20-trinor-cis-13-;
cis-4,5-didehydro-16-phenoxy-17,18,19,20-tetranor-cis-13-;
cis-4,5-didehydro-15-methyl-16-phenoxy-17,18,19,20-tetranor-cis-13-;
cis-4,5-didehydro-16-(m-trifluoromethylphenoxy)-17,18,19,20-tetranor-cis-13-;
cis-4,5-didehydro-16-(m-chlorophenoxy)-17,18,19,20-tetranor-cis-13-;
cis-4,5-didehydro-16-(p-fluorophenoxy)-17,18,19,20-tetranor-cis-13-;
cis-4,5-didehydro-16-phenoxy-18,19,20-trinor-cis-13-;
cis-4,5-didehydro-15-methyl-16-phenoxy-18,19,20-trinor-cis-13-;
cis-4,5-didehydro-16-methyl-16-phenoxy-18,19,20-trinor-cis-13-;
5-oxa-;
5-oxa-15-methyl-;
5-oxa-16-methyl-;
5-oxa-16,16-dimethyl-;
5-oxa-16-fluoro-;
5-oxa-16,16-difluoro-;
5-oxa-15-methyl-16,16-difluoro-;
5-oxa-17-phenyl-18,19,20-trinor-;
5-oxa-17-(m-trifluoromethylphenyl)-18,19,20-trinor-;
5-oxa-17-(m-chlorophenyl)-18,19,20-trinor-;
5-oxa-17-(p-fluorophenyl)-18,19,20-trinor-;
5-oxa-15-methyl-17-phenyl-18,19,20-trinor-;
5-oxa-16-methyl-17-phenyl-18,19,20-trinor-;
5-oxa-16,16-dimethyl-17-phenyl-18,19,20-trinor-;
5-oxa-16-fluoro-17-phenyl-18,19,20-trinor-;
5-oxa-16,16-difluoro-17-phenyl-18,19,20-trinor-;
5-oxa-15-methyl-16,16-difluoro-17-phenyl-18,19,20-trinor-;
5-oxa-16-phenoxy-17,18,19,20-tetranor-;
5-oxa-16-(m-trifluoromethylphenoxy)-17,18,19,20-tetranor-;
5-oxa-16-(m-chlorophenoxy)-17,18,19,20-tetranor-;
5-oxa-16-(p-fluorophenoxy)-17,18,19,20-tetranor-;
5-oxa-15-methyl-16-phenoxy-17,18,19,20-tetranor-;
5-oxa-16-phenoxy-18,19,20-trinor-;
5-oxa-15-methyl-16-phenoxy-18,19,20-trinor-;
5-oxa-16-methyl-16-phenoxy-18,19,20-trinor-;
5-oxa-13,14-didehydro;
5-oxa-15-methyl-13,14-didehydro-;
5-oxa-16-methyl-13,14-didehydro-;
5-oxa-16,16-dimethyl-13,14-didehydro-;
5-oxa-16-fluoro-13,14-didehydro-;
5-oxa-16,16-difluoro-13,14-didehydro-;
5-oxa-15-methyl-16,16-difluoro-13,14-didehydro-;
5-oxa-17-phenyl-18,19,20-trinor-13,14-didehydro-;
5-oxa-17-(m-trifluoromethylphenyl)-18,19,20-trinor-13,14-didehydro-;
5-oxa-17-(m-chlorophenyl)-18,19,20-trinor-13,14-didehydro-;
5-oxa-17-(p-fluorophenyl)-18,19,20-trinor-13,14-didehydro-;
5-oxa-15-methyl-17-phenyl-18,19,20-trinor-13,14-didehydro-;
5-oxa-16-methyl-17-phenyl-18,19,20-trinor-13,14-didehydro-;
5-oxa-16,16-dimethyl-17-phenyl-18,19,20-trinor-13,14-didehydro-;
5-oxa-16-fluoro-17-phenyl-18,19,20-trinor-13,14-didehydro-;
5-oxa-16,16-difluoro-17-phenyl-18,19,20-trinor-13,14-dihydro-;
5-oxa-16-phenoxy-17,18,19,20-tetranor-13,14-didehydro-;
5-oxa-16-(m-trifluoromethylphenoxy)-17,18,19,20-tetranor-13,14-didehydro-;
5-oxa-16-(m-chlorophenoxy)-17,18,19,20-tetranor-13,14-didehydro-;
5-oxa-15-methyl-16-phenoxy-17,18,19,20-tetranor-13,14-didehydro-;
5-oxa-16-phenoxy-18,19,20-trinor-13,14-didehydro-;
5-oxa-16-methyl-16-phenoxy-18,19,20-trinor-13,14-didehydro-;
5-oxa-13,14-dihydro-;
5-oxa-15-methyl-13,14-dihydro-;
5-oxa-16-methyl-13,14-dihydro-;
5-oxa-16,16-dimethyl-13,14-dihydro-;
5-oxa-16-fluoro-13,14-dihydro-;
5-oxa-16,16-difluoro-13,14-dihydro-;
5-oxa-15-methyl-16,16-tetrafluoro-13,14-dihydro-;
5-oxa-17-phenyl-18,19,20-trinor-13,14-dihydro-;
5-oxa-17-(m-trifluoromethylphenyl)-18,19,20-trinor-13,14-dihydro-;
5-oxa-17-(m-chlorophenyl)-18,19,20-trinor-13,14-dihydro-;
5-oxa-17-(p-fluorophenyl)-18,19,20-trinor-13,14-dihydro-;
5-oxa-15-methyl-17-(p-fluorophenyl)-18,19,20-trinor-13,14-dihydro-;
5-oxa-15-methyl-17-phenyl-18,19,20-trinor-13,14-dihydro-;

5-oxa-16-methyl-17-phenyl-18,19,20-trinor-13,14-dihydro-;
5-oxa-16,16-dimethyl-17-phenyl-18,19,20-trinor-13,14-dihydro-;
5-oxa-fluoro-17-phenyl-18,19,20-dihydro-;
5-oxa-16,16-difluoro-17-phenyl-18,19,20-dihydro-;
5-oxa-16-phenoxy-17,18,19,20-tetranor-13,14-dihydro-;
5-oxa-16-(m-trifluoromethylphenoxy)-17,18,19,20-tetranor-13,14-dihydro-;
5-oxa-16-(m-chlorophenoxy)-17,18,19,20-tetranor-13,14-dihydro-;
5-oxa-16-(p-fluorophenoxy)-17,18,19,20-tetranor-13,14-dihydro-;
5-oxa-15-methyl-16-phenoxy-17,18,19,20-tetranor-13,14-dihydro-;
5-oxa-16-phenoxy-18,19,20-trinor-13,14-dihydro-;
5-oxa-15-methyl-16-phenoxy-18,19,20-trinor-13,14-dihydro-;
5-oxa-16-methyl-16-phenoxy-18,19,20-trinor-13,14-dihydro-;
5-oxa-cis-13-;
5-oxa-15-methyl-cis-13-;
5-oxa-16-methyl-cis-13-;
5-oxa-16,16-dimethyl-cis-13-;
5-oxa-16-fluoro-cis-13-;
5-oxa-16,16-difluoro-cis-13-;
5-oxa-15-methyl-16,16-difluoro-cis-13-;
5-oxa-17-phenyl-18,19,20-trinor-cis-13-;
5-oxa-17-(m-trifluoromethylphenyl)-18,19,20-trinor-cis-13-;
5-oxa-17-(m-chlorophenyl)-18,19,20-trinor-cis-13-;
5-oxa-17-(p-fluorophenyl)-18,19,20-trinor-cis-13-;
5-oxa-15-methyl-17-phenyl-18,19,20-trinor-cis-13-;
5-oxa-16-methyl-17-phenyl-18,19,20-trinor-cis-13-;
5-oxa-16,16-dimethyl-17-phenyl-18,19,20-trinor-cis-13-;
5-oxa-16-fluoro-17-phenyl-18,19,20-trinor-cis-13-;
5-oxa-16,16-difluoro-17-phenyl-18,19,20-trinor-cis-13-;
5-oxa-15-methyl-16,16-difluoro-17-phenyl-18,19,20-trinor-cis-13-;
5-oxa-16-phenoxy-17,18,19,20-tetranor-cis-13-;
5-oxa-15-methyl-16-phenoxy-17,18,19,20-tetranor-cis-13-;
5-oxa-16-(m-trifluoromethylphenoxy)-17,18,19,20-tetranor-cis-13-;
5-oxa-16-(m-chlorophenoxy)-17,18,19,20-tetranor-cis-13-;
5-oxa-16-(p-fluorophenoxy)-17,18,19,20-tetranor-cis-13-;
5-oxa-16-phenoxy-18,19,20-trinor-cis-13-;
5-oxa-15-methyl-16-phenoxy-18,19,20-trinor-cis-13-;
5-oxa-16-methyl-16-phenoxy-18,19,20-trinor-cis-13-;
4-oxa-;
4-oxa-15-methyl-;
4-oxa-16-methyl-;
4-oxa-16,16-dimethyl-;
4-oxa-16-fluoro-;
4-oxa-16,16-difluoro-;
4-oxa-15-methyl-16,16-difluoro-;
4-oxa-17-phenyl-18,19,20-trinor-;
4-oxa-17-(m-trifluoromethylphenyl)-18,19,20-trinor-;
4-oxa-17-(m-chlorophenyl)-18,19,20-trinor-;
4-oxa-17-(p-fluorophenyl)-18,19,20-trinor-;
4-oxa-15-methyl-17-phenyl-18,19,20-trinor-;
4-oxa-16-methyl-17-phenyl-18,19,20-trinor-;
4-oxa-16,16-dimethyl-17-phenyl-18,19,20-trinor-;
4-oxa-16-fluoro-17-phenyl-18,19,20-trinor-;
4-oxa-16,16-difluoro-17-phenyl-18,19,20-trinor-;
4-oxa-15-methyl-16,16-difluoro-17-phenyl-18,19,20-trinor-;
4-oxa-16-phenoxy-17,18,19,20-tetranor-;
4-oxa-16-(m-trifluoromethylphenoxy)-17,18,19,20-tetranor-;
4-oxa-16-(m-chlorophenoxy)-17,18,19,20-tetranor-;
4-oxa-16-(p-fluorophenoxy)-17,18,19,20-tetranor-;
4-oxa-15-methyl-16-phenoxy-17,18,19,20-tetranor-;
4-oxa-16-phenoxy-18,19,20-trinor-;
4-oxa-15-methyl-16-phenoxy-18,19,20-trinor-;
4-oxa-16-phenoxy-18,19,20-trinor-;
4-oxa-16-methyl-13,14-didehydro-;
4-oxa-16,16-dimethyl-13,14-didehydro-;
4-oxa-16-fluoro-13,14-didehydro-;
4-oxa-16,16-difluoro-13,14-didehydro-;
4-oxa-15-methyl-16,16-difluoro-13,14-didehydro-;
4-oxa-17-phenyl-18,19,20-trinor-13,14-didehydro-;
4-oxa-15-methyl-17-phenyl-18,19,20-trinor-13,14-didehydro-;
4-oxa-17-(m-trifluoromethylphenyl)-18,19,20-trinor-13,14-didehydro-;
4-oxa-17-(m-chlorophenyl)-18,19,20-trinor-13,14-didehydro-;
4-oxa-17-(p-fluorophenyl)-18,19,20-trinor-13,14-didehydro-;
4-oxa-16-methyl-17-phenyl-18,19,20-trinor-13,14-didehydro-;
4-oxa-16,16-dimethyl-17-phenyl-18,19,20-trinor-13,14-didehydro-;
4-oxa-16-fluoro-17-phenyl-18,19,20-trinor-13,14-didehydro-;
4-oxa-16,16-difluoro-17-phenyl-18,19,20-trinor-13,14-dihydro-;
4-oxa-16-phenoxy-17,18,19,20-tetranor-13,14-didehydro-;
4-oxa-16-(m-trifluoromethylphenoxy)-17,18,19,20-tetranor-13,14-didehydro-;
4-oxa-16-(m-chlorophenoxy)-17,18,19,20-tetranor-13,14-didehydro-;
4-oxa-15-methyl-16-phenoxy-17,18,19,20-tetranor-13,14-didehydro-;
4-oxa-15-methyl-17-phenyl-18,19,20-trinor-13,14-dihydro-;
4-oxa-17-(m-trifluoromethylphenyl)-18,19,20-trinor-13,14-dihydro-;
4-oxa-17-(m-chlorophenyl)-18,19,20-trinor-13,14-dihydro-;
4-oxa-17-(p-fluorophenyl)-18,19,20-trinor-13,14-dihydro-;
4-oxa-15-methyl-17-(p-fluorophenyl)-18,19,20-trinor-13,14-dihydro-;
4-oxa-16-methyl-17-phenyl-18,19,20-trinor-13,14-dihydro-;
4-oxa-16,16-dimethyl-17-phenyl-18,19,20-trinor-13,14-dihydro-;
4-oxa-16-fluoro-17-phenyl-18,19,20-dihydro-;
4-oxa-16,16-difluoro-17-phenyl-18,19,20-dihydro-;
4-oxa-16-phenoxy-17,18,19-tetranor-13,14-dihydro-;
4-oxa-16-(m-trifluoromethylphenoxy)-17,18,19,20-tetranor-13,14-dihydro-;
4-oxa-16-(m-chlorophenoxy)-17,18,19,20-tetranor-13,14-dihydro-;
4-oxa-16-(p-fluorophenoxy)-17,18,19,20-tetranor-13,14-dihydro-;
4-oxa-15-methyl-16-phenoxy-17,18,19,20-tetranor-13,14-dihydro-;
4-oxa-16-phenoxy-18,19,20-trinor-13,14-dihydro-;

4-oxa-15-methyl-16-phenoxy-18,19,20-trinor-13,14-dihydro-;
4-oxa-16-methyl-16-phenoxy-18,19,20-trinor-13,14-dihydro-;
4-oxa-cis-13-;
4-oxa-15-methyl-cis-13-;
4-oxa-16-methyl-cis-13-;
4-oxa-16,16-dimethyl-cis-13-;
4-oxa-16-fluoro-cis-13-;
4-oxa-16,16-difluoro-cis-13-;
4-oxa-15-methyl-16,16-difluoro-cis-13-;
4-oxa-17-phenyl-18,19,20-trinor-cis-13-;
4-oxa-17-(m-trifluoromethylphenyl)-18,19,20-trinor-cis-13-;
4-oxa-17-(m-chlorophenyl)-18,19,20-trinor-cis-13-;
4-oxa-17-(p-fluorophenyl)-18,19,20-trinor-cis-13-;
4-oxa-15-methyl-17-phenyl-18,19,20-trinor-cis-13-;
4-oxa-16-methyl-17-phenyl-18,19,20-trinor-cis-13-;
4-oxa-16,16-dimethyl-17-phenyl-18,19,20-trinor-cis-13-;
4-oxa-16-fluoro-17-phenyl-18,19,20-trinor-cis-13-;
4-oxa-16,16-difluoro-17-phenyl-18,19,20-trinor-cis-13-;
4-oxa-15-methyl-16,16-difluoro-17-phenyl-18,19,20-trinor-cis-13-;
4-oxa-16-phenoxy-17,18,19,20-tetranor-cis-13-;
4-oxa-16-(m-trifluoromethylphenoxy)-17,18,19,20-tetranor-cis-13-;
4-oxa-16-(m-chlorophenoxy)-17,18,19,20-tetranor-cis-13-;
4-oxa-16-(p-fluorophenoxy)-17,18,19,20-tetranor-cis-13-;
4-oxa-15-methyl-16-phenoxy-17,18,19,20-tetranor-cis-13-;
4-oxa-16-phenoxy-18,19,20-trinor-cis-13-;
4-oxa-15-methyl-16-phenoxy-18,19,20-trinor-cis-13-;
4-oxa-16-methyl-16-phenoxy-18,19,20-trinor-cis-13-;
trans-2,3-didehydro-;
trans-2,3-didehydro-15-methyl-;
trans-2,3-didehydro-16-methyl-;
trans-2,3-didehydro-16,16-dimethyl-;
trans-2,3-didehydro-16-fluoro-;
trand-2,3-didehydro-16,16-difluoro-;
trans-2,3-didehydro-15-methyl-16,16-difluoro-;
trans-2,3-didehydro-17-phenyl-18,19,20-trinor-;
trans-2,3-didehydro-17-(m-trifluoromethylphenyl)-18,19,20-trinor-;
trans-2,3-didehydro-17-(m-chlorophenyl)-18,19,20-trinor-;
trans-2,3-didehydro-17-(p-fluorophenyl)-18,19,20-trinor-;
trans-2,3-didehydro-15-methyl-17-phenyl-18,19,20-trinor-;
trans-2,3-didehydro-16-methyl-17-phenyl-18,19,20-trinor-;
trans-2,3-didehydro-16,16-dimethyl-17-phenyl-18,19,20-trinor-;
trans-2,3-didehydro-16-fluoro-17-phenyl-18,19,20-trinor-;
trans-2,3-didehydro-16,16-difluoro-17-phenyl-18,19,20-trinor-;
trans-2,3-didehydro-15-methyl-16,16-difluoro-17-phenyl-18,19,20-trinor-;
trans-2,3-didehydro-16-phenoxy-17,18,19,20-tetranor-;
trans-2,3-didehydro-15-methyl-16-phenoxy-17,18,19,20-tetranor-;
trans-2,3-didehydro-16-(m-trifluoromethylphenoxy)-17,18,19,20-tetranor-;
trans-2,3-didehydro-16-(m-chlorophenoxy)-17,18,19,20-tetranor-;
trans-2,3-didehydro-16-(p-fluorophenoxy)-17,18,19,20-tetranor-;
trans-2,3-didehydro-16-phenoxy-18,19,20-trinor-;
trans-2,3-didehydro-15-methyl-16-phenoxy-18,19,20-trinor-;
trans-2,3-didehydro-16-methyl-16-phenoxy-18,19,20-trinor-;
trans-2,3-didehydro-16-methyl-13,14-didehydro-;
trans-2,3-didehydro-16,16-dimethyl-13,14-didehydro-;
trans-2,3-didehydro-16-fluoro-13,14-didehydro-;
trans-2,3-didehydro-16,16-difluoro-13,14-didehydro-;
trans-2,3-didehydro-15-methyl-16,16-difluoro-13,14-didehydro-;
trans-2,3-didehydro-17-phenyl-18,19,20-trinor-13,14-didehydro-;
trans-2,3-didehydro-17-(m-trifluoromethylphenyl)-18,19,20-trinor-13,14-didehydro-;
trans-2,3-didehydro-17-(m-chlorophenyl)-18,19,20-trinor-13,14-didehydro-;
trans-2,3-didehydro-17-(p-fluorophenyl)-18,19,20-trinor-13,14-didehydro-;
trans-2,3-didehydro-15-methyl-17-phenyl-18,19,20-trinor-13,14-didehydro-;
trans-2,3-didehydro-16-methyl-17-phenyl-18,19,20-trinor-13,14-didehydro-;
trans-2,3-didehydro-16,16-dimethyl-17-phenyl-18,19,20-trinor-13,14-didehydro-;
trans-2,3-didehydro-16-fluoro-17-phenyl-18,19,20-trinor-13,14-didehydro-;
trans-2,3-didehydro-16,16-difluoro-17-phenyl-18,19,20-trinor-13,14-didehydro-;
trans-2,3-didehydro-16-phenoxy-17,18,19,20-tetranor-13,14-didehydro-;
trans-2,3-didehydro-15-methyl-16-phenoxy-17,18,19,20-tetranor-13,14-didehydro-;
trans-2,3-didehydro-16-(m-trifluoromethylphenoxy)-17,18,19,20-tetranor-13,14-didehydro-;
trans-2,3-didehydro-16-(m-chlorophenoxy)-17,18,19,20-tetranor-13,14-didehydro-;
trans-2,3-didehydro-16-phenoxy-18,19,20-trinor-13,14-didehydro-;
trans-2,3-didehydro-16-methyl-16-phenoxy-18,19,20-trinor-13,14-didehydro-;
trans-2,3-didehydro-13,14-dihydro-;
trans-2,3-didehydro-15-methyl-13,14-dihydro-;
trans-2,3-didehydro-16-methyl-13,14-dihydro-;
trans-2,3-didehydro-16,16-dimethyl-13,14-dihydro-;
trans-2,3-didehydro-16-fluoro-13,14-dihydro-;
trans-2,3-didehydro-16,16-difluoro-13,14-dihydro-;
trans-2,3-didehydro-17-phenyl-18,19,20-trinor-13,14-didehydro-;
trans-2,3-didehydro-15-methyl-17-phenyl-18,19,20-trinor-13,14-dihydro-;
trans-2,3-didehydro-17-(m-trifluoromethylphenyl)-18,19,20-trinor-13,14-dihydro-;
trans-2,3-didehydro-17-(m-chlorophenyl)-18,19,20-trinor-13,14-dihydro-;
trans-2,3-didehydro-17-(p-fluorophenyl)-18,19,20-trinor-13,14-dihydro-;
trans-1,3-didehydro-15-methyl-16,16-tetrafluoro-13,14-didehydro-;
trans-2,3-didehydro-15-methyl-17-(p-fluorophenyl)-18,19,20-trinor-13,14-dihydro-;
trans-2,3-didehydro-16-methyl-17-phenyl-18,19,20-trinor-13,14-dihydro-;
trans-2,3-didehydro-16,16-dimethyl-17-phenyl-18,19,20-trinor-13,14-dihydro-;

trans-2,3-didehydro-16-fluoro-17-phenyl-18,19,20-dihydro-;
trans-2,3-didehydro-16,16-difluoro-17-phenyl-18,19,20-trinor-dihydro-;
trans-2,3-didehydro-16-phenoxy-17,18,19,20-tetranor-13,14-dihydro-;
trans-2,3-didehydro-15-methyl-16-phenoxy-17,18,19,20-tetranor-13,14-dihydro-;
trans-2,3-didehydro-16-(m-trifluoromethylphenoxy)-17,18,19,20-tetranor-13,14-dihydro-;
trans-2,3-didehydro-16-(m-chlorophenoxy)-17,18,19,20-tetranor-13,14-dihydro-;
trans-2,3-didehydro-16-(p-fluorophenoxy)-17,18,19,20-tetranor-13,14-dihydro-;
trans-2,3-didehydro-16-phenoxy-18,19,20-trinor-13,14-didehydro-;
trans-1,3-didehydro-15-methyl-16-phenoxy-18,19,20-trinor-13,14-dihydro-;
trans-2,3-didehydro-16-methyl-phenoxy-18,19,20-trinor-13,14-dihydro-;
trans-2,3-didehycro-cis-13-;
trans-2,3-didehydro-15-methyl-cis-13-;
trans-2,3-didehydro-16-methyl-cis-13-;
trans-2,3-didehydro-16,16-dimethyl-cis-13-;
trans-2,3-didehydro-16-fluoro-cis-13-;
trans-2,3-didehydro-16,16-difluoro-cis-13-;
trans-2,3-didehydro-15-methyl-16,16-difluoro-cis-13-;
trans-2,3-didehydro-17-phenyl-18,19,20-trinor-cis-13-;
trans-2,3-didehydro-17-(m-trifluoromethylphenyl)-18,19,20-trinor-cis-13-;
trans-2,3-didehydro-17-(m-chlorophenyl)-18,19,20-trinor-cis-13-;
trans-2,3-didehydro-17-(p-fluorophenyl)-18,19,20-trinor-cis-13-;
trans-2,3-didehydro-15-methyl-17-phenyl-18,19,20-trinor-cis-13-;
trans-2,3-didehydro-16-methyl-17-phenyl-18,19,20-trinor-cis-13-;
trans-2,3-didehydro-16,16-dimethyl-17-phenyl-18,19,20-trinor-cis-13-;
trans-2,3-didehydro-16-fluoro-17-phenyl-18,19,20-trinor-cis-13-;
trans-2,3-didehydro-16,16-difluoro-17-phenyl-18,19,20-trinor-cis-13-;
trans-2,3-didehydro-15-methyl-16,16-difluoro-17-phenyl-18,19,20-trinor-cis-13-;
trans-2,3-didehydro-16-phenoxy-17,18,19,20-tetranor-cis-13-;
trans-2,3-didehydro-16-(m-trifluoromethylphenoxy)-17,18,19,20-tetranor-cis-13-;
trans-2,3-didehydro-16-(m-chlorophenoxy)-17,18,19,20-tetranor-cis-13-;
trans-2,3-didehydro-16-(p-fluorophenoxy)-17,18,19,20-tetranor-cis-13-;
trans-2,3-didehydro-15-methyl-16-phenoxy-17,18,19,20-tetranor-cis-13-;
trans-2,3-didehydro-16-phenoxy-18,19,20-trinor-cis-13-;
trans-2,3-didehydro-15-methyl-16-phenoxy-18,19,20-trinor-cis-13-; and
trans-2,3-didehydro-16-methyl-16-phenoxy-18,19,20-trinor-cis-13-.

formulas

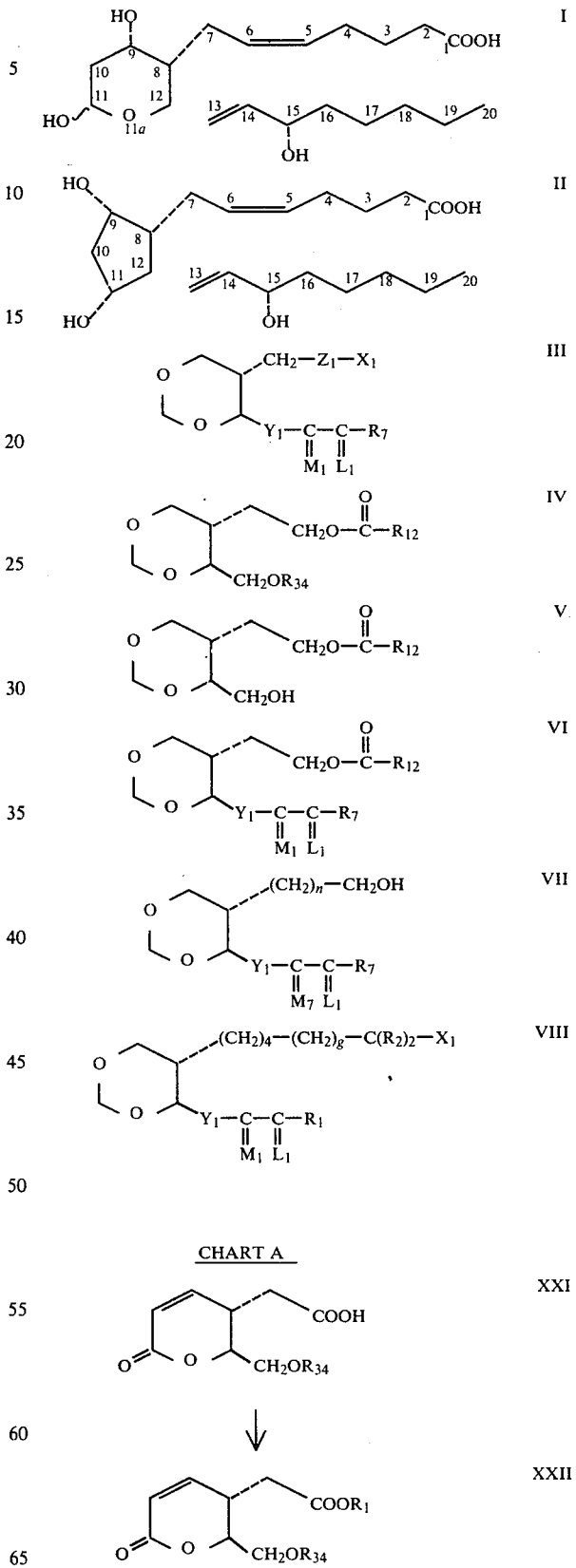

-continued
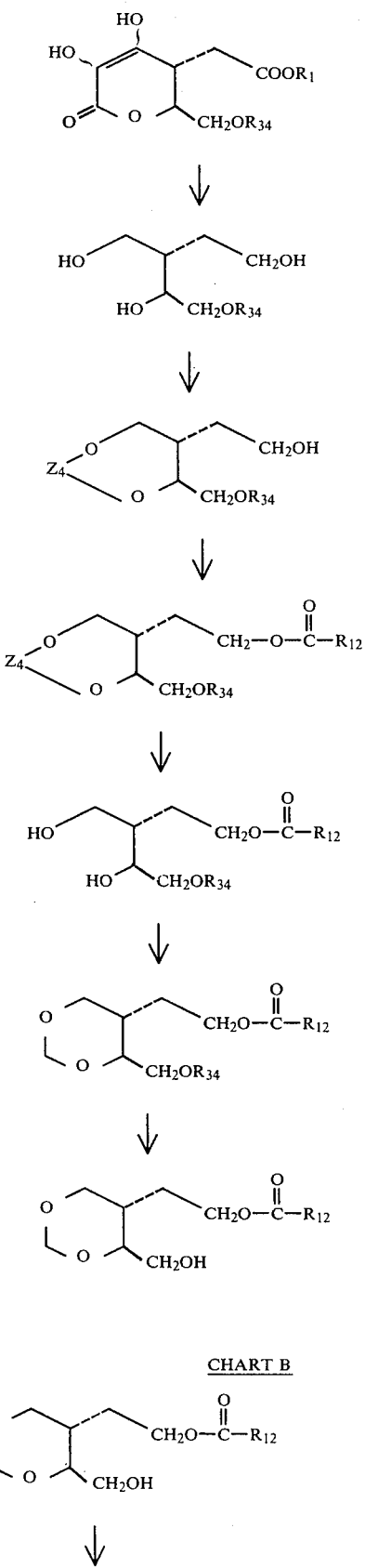
CHART B
-continued
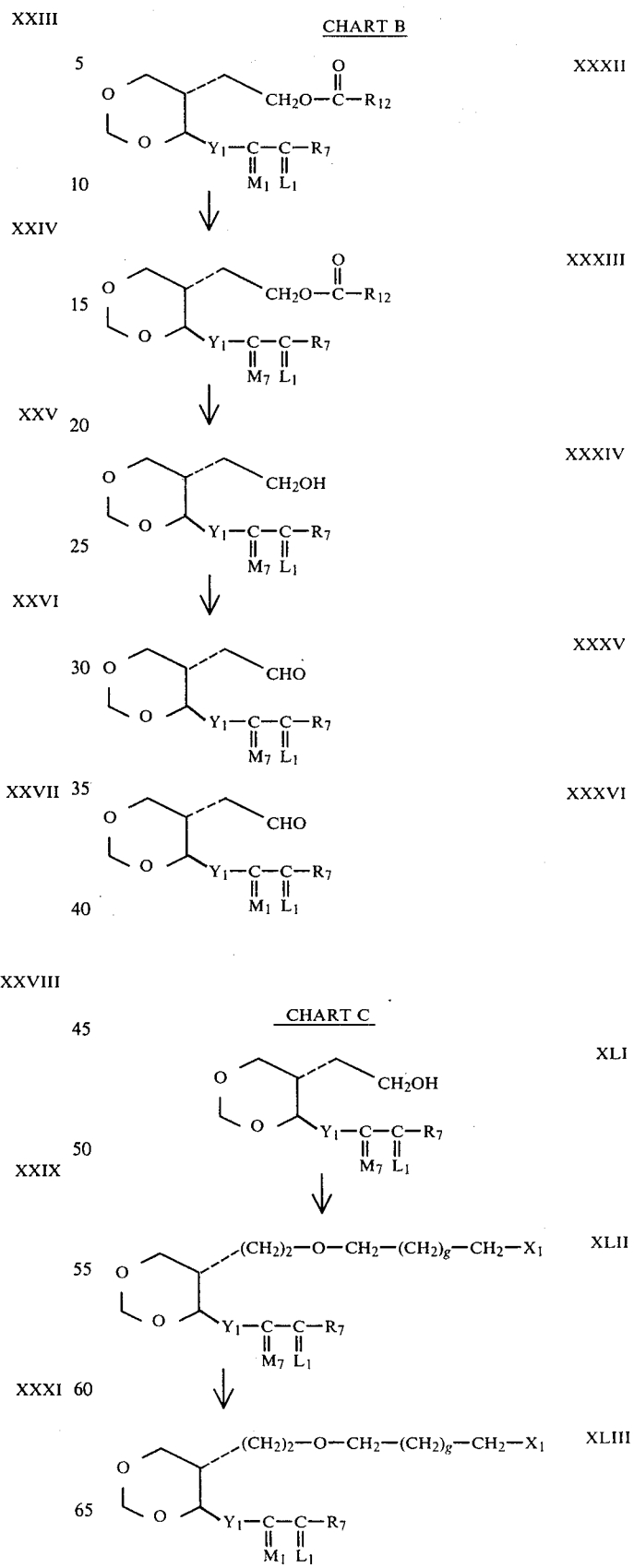
CHART C

CHART D
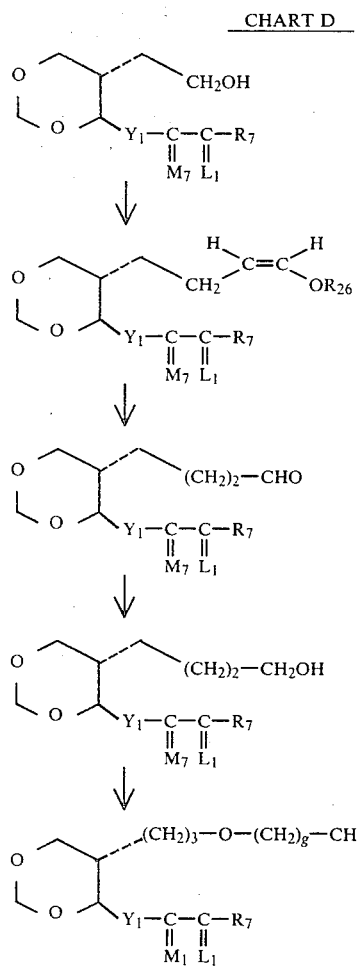
CHART E
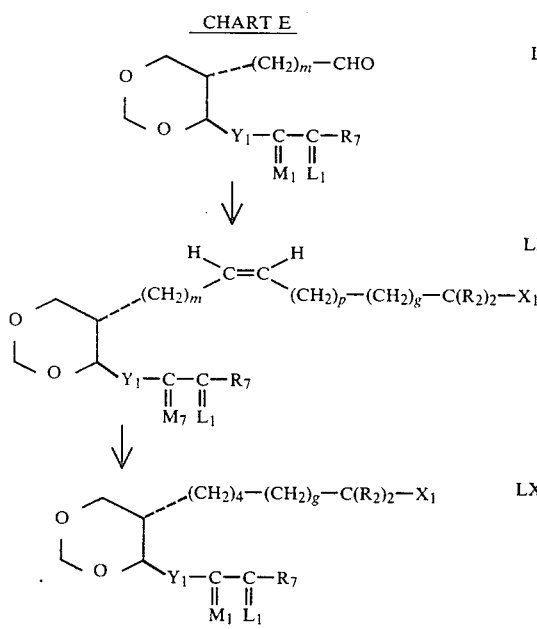
CHART F
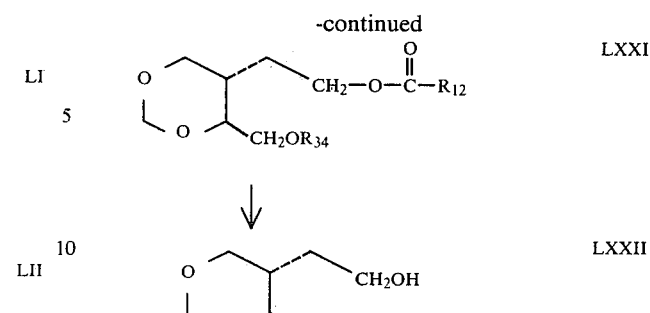
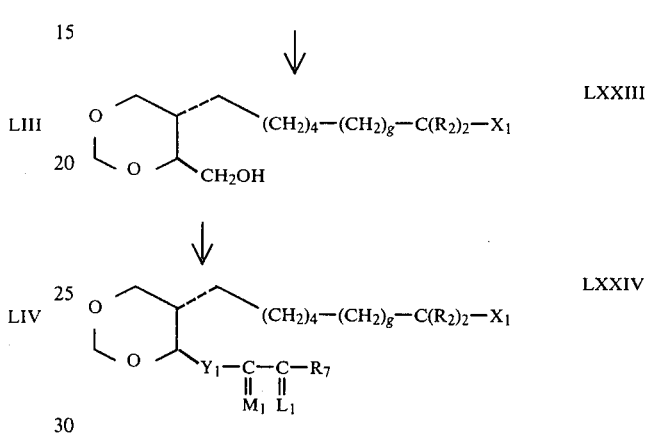
CHART G
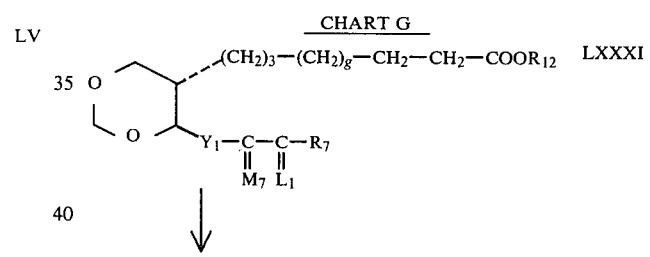
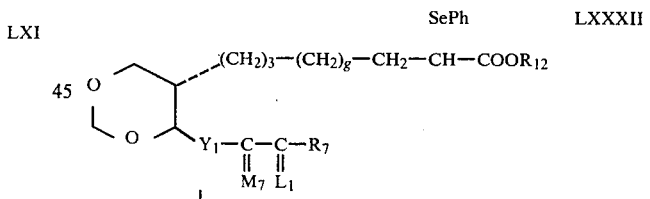
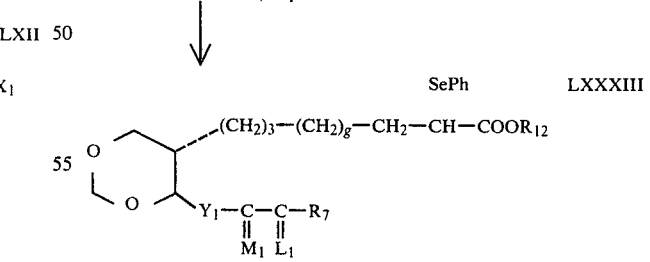
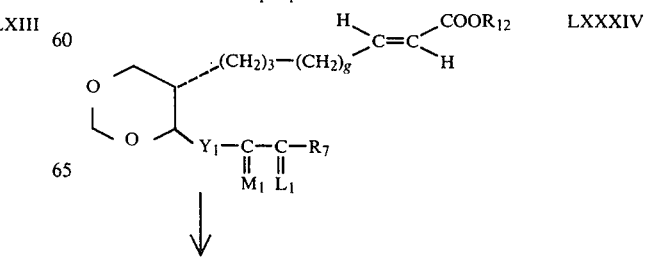

-continued
CHART G

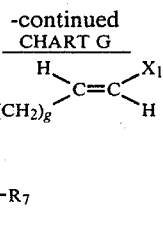
LXXXV

I claim:
1. A thromboxane analog of formula III,

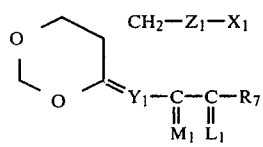
III wherein $Y_1$ is
(1) trans—CH=CH—,
(2) cis—CH=CH—,
(3) —CH$_2$CH$_2$—, or
(4) —C≡C—,
wherein $M_1$ is α-$R_5$:β-OH, α-OH:β-$R_5$, or α-H:β-H, wherein $R_5$ is hydrogen or methyl;
wherein $L_1$ is α-$R_3$:β-$R_4$, α-$R_4$:β-$R_3$, or a mixture of α-$R_3$:β-$R_4$ and β-$R_3$:α-$R_4$, wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$—O—(CH$_2$)$_g$—CH$_2$—, or
(8) trans—CH$_2$—(CH$_2$)$_g$—CH$_2$—CH=CH—;
wherein g is one, 2, or 3;
wherein $R_7$ is
(1) —(CH$_2$)$_m$—CH$_3$, wherein m is an integer from one to 5, inclusive;
(2) phenoxy;
(3) phenoxy substituted by one, two, or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two, or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $X_1$ is
(1) —COOR$_1$, wherein $R_1$ is
(a) hydrogen;
(b) alkyl of one to 12 carbon atoms, inclusive;
(c) cycloalkyl of 3 to 10 carbon atoms, inclusive;
(d) aralkyl of 7 to 12 carbon atoms, inclusive;
(e) phenyl;
(f) phenyl substituted with one, two, or three chloro or alkyl of one to 3 carbon atoms;
(g) phenyl substituted in the para position by
(i) —NH—CO—R$_{25}$
(ii) —CO—R$_{26}$
(iii) —O—CO—R$_{27}$
(iv) —CH=N—NH—CO—NH$_2$
wherein $R_{25}$ is methyl, phenyl, acetamidophenyl, benzamidophenyl, or —NH$_2$; $R_{26}$ is methyl, phenyl, —NH$_2$, or methoxy; and $R_{27}$ is phenyl or acetamidophenyl, inclusive, or a pharmacologically acceptable salt thereof when $R_1$ is hydrogen;
(2) —CH$_2$OH; or
(3) —CH$_2$NL$_2$L$_3$, wherein $L_2$ and $L_3$ are hydrogen or alkyl of one to 4 carbon atoms, inclusive, being the same or different, or a pharmacologically acceptable acid addition salt thereof wherein $X_1$ is —CH$_2$NL$_2$L$_3$.
2. 9,11-Dideoxy-10-oxa-TXB$_2$.
3. 9,11,15-Trideoxy-10-oxa-TXB$_2$.

* * * * *

UNITED STATES PATENT OFFICE
CERTIFICATE OF CORRECTION

Patent No. 4,243,592  Dated 6 January 1981

Inventor(s) Douglas R. Morton, Jr.

It is certified that error appears in the above-identified patent and that said Letters Patent are hereby corrected as shown below:

Column 5, lines 24-25, "comounds" should read -- compounds --;
Column 9, line 3, "Exaples" should read -- Examples --; line 50, "2-dluoro-" should read -- 2-fluoro- --;
Column 10, line 27, "pain in attained" should read -- pain is attained --
Column 12, lines 3-4, "cyclopendylamine" should read -- cyclopentylamine --; line 24, "basis amino" should read -- basic amino --;
Column 18, line 10, "$Y_1$ is -C≡C-" should read -- $Y_1$ is -C≡C- --;
Column 50, lines 2-16, the formulas I and II should read as follows:

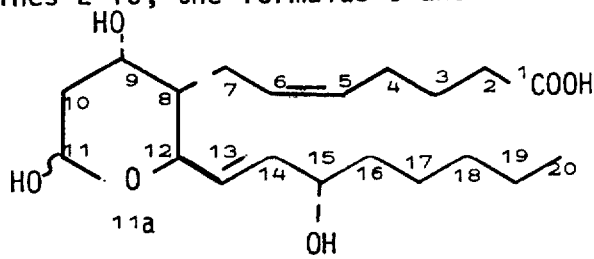

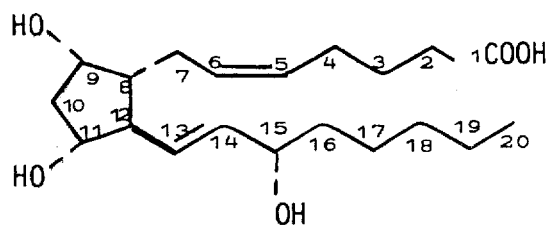

Column 51, lines 2-8 - - - - Formula XXIII should read:

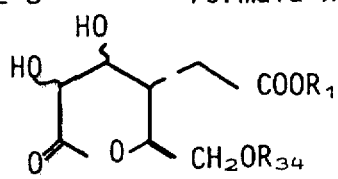

UNITED STATES PATENT OFFICE
CERTIFICATE OF CORRECTION

Page 2 of 3 Pages

Patent No. 4,243,592          Dated 6 January 1981

Inventor(s) Douglas R. Morton, Jr.

It is certified that error appears in the above-identified patent and that said Letters Patent are hereby corrected as shown below:

Column 53, lines 10-16, Formula LII should read as follows:

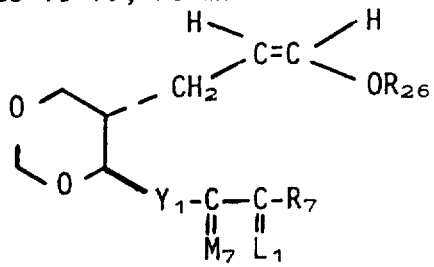

Column 53, lines 17-23, Formula LIII should read as follows:

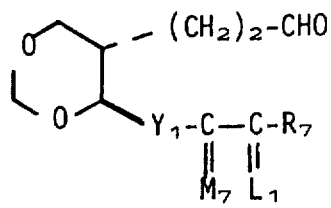

Column 53, lines 25-30, Formula LIV should read as follows:

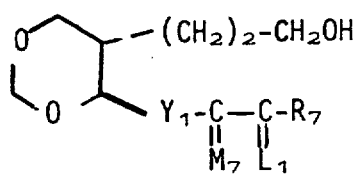

UNITED STATES PATENT OFFICE
CERTIFICATE OF CORRECTION

Patent No. 4,243,592　　　　　　　Dated 6 January 1981

Inventor(s) Douglas R. Morton, Jr.

It is certified that error appears in the above-identified patent and that said Letters Patent are hereby corrected as shown below:

Column 54, lines 43-58, that portion of Formulas LXXXII and LXXIII reading　　　　　　　　　　　　　　should read

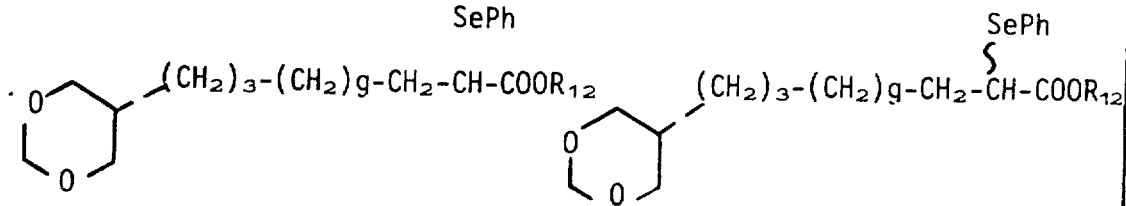

Column 55, lines 13-20, the formula should read as follows:

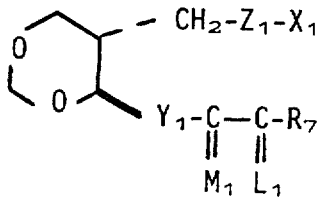

Signed and Sealed this

Fourteenth Day of September 1982

[SEAL]

*Attest:*

*Attesting Officer*　　　　　GERALD J. MOSSINGHOFF
　　　　　　　　　　　　　*Commissioner of Patents and Trademarks*